United States Patent
Fright et al.

(10) Patent No.: US 10,827,970 B2
(45) Date of Patent: Nov. 10, 2020

(54) METHOD OF MONITORING A SURFACE FEATURE AND APPARATUS THEREFOR

(71) Applicant: ARANZ Healthcare Limited, Christchurch (NZ)

(72) Inventors: William Richard Fright, Christchurch (NZ); Mark Arthur Nixon, Christchurch (NZ); Bruce Clinton McCallum, Lyttelton (NZ); James Telford George Preddey, Einsiedeln (CH)

(73) Assignee: ARANZ Healthcare Limited, Christchurch (NZ)

( * ) Notice: Subject to any disclaimer, the term of this patent is extended or adjusted under 35 U.S.C. 154(b) by 405 days.

(21) Appl. No.: 15/938,921

(22) Filed: Mar. 28, 2018

(65) Prior Publication Data

US 2018/0214071 A1    Aug. 2, 2018

Related U.S. Application Data

(63) Continuation of application No. 15/338,216, filed on Oct. 28, 2016, now Pat. No. 9,955,910, which is a
(Continued)

(30) Foreign Application Priority Data

Oct. 14, 2005    (NZ) ........................................ 543003

(51) Int. Cl.
*A61B 5/00* (2006.01)
*A61B 5/107* (2006.01)
(Continued)

(52) U.S. Cl.
CPC ............ *A61B 5/445* (2013.01); *A61B 5/0013* (2013.01); *A61B 5/0022* (2013.01);
(Continued)

(58) Field of Classification Search
None
See application file for complete search history.

(56) References Cited

U.S. PATENT DOCUMENTS

| 3,259,612 A | 7/1966 | Peter |
| 3,335,716 A | 8/1967 | Alt et al. |

(Continued)

FOREIGN PATENT DOCUMENTS

| DE | 2642841 | 3/1978 |
| DE | 3420588 | 12/1984 |

(Continued)

OTHER PUBLICATIONS

Ahn et al., "Advances in Wound Photography and Assessment Methods," Advances in Skin & Wound Care, Feb. 2008, pp. 85-93.
(Continued)

*Primary Examiner* — Samah A Beg
(74) *Attorney, Agent, or Firm* — Perkins Coie LLP

(57) ABSTRACT

Dimensions of a surface feature are determined by capturing an image of the surface feature and determining a scale associated with the image. Structured light may be projected onto the surface, such that the position of structured light in the captured image allows determination of scale. A non-planar surface may be unwrapped. The surface may alternatively be projected into a plane to correct for the scene being tilted with respect to the camera axis. A border of the surface feature may be input manually by a user. An apparatus and system for implementing the method are also disclosed.

34 Claims, 7 Drawing Sheets

Related U.S. Application Data continuation of application No. 15/164,793, filed on May 25, 2016, now abandoned, which is a continuation of application No. 14/272,719, filed on May 8, 2014, now Pat. No. 9,377,295, which is a continuation of application No. 12/083,491, filed as application No. PCT/NZ2006/000262 on Oct. 13, 2006, now Pat. No. 8,755,053.

(51) Int. Cl.

| | | |
|---|---|---|
| G06T 7/00 | (2017.01) | |
| A61B 5/01 | (2006.01) | |
| A61B 5/145 | (2006.01) | |
| A61B 8/08 | (2006.01) | |
| G01B 11/00 | (2006.01) | |
| G01B 11/02 | (2006.01) | |
| G01B 11/22 | (2006.01) | |
| G01B 11/28 | (2006.01) | |
| G01B 11/14 | (2006.01) | |
| H04N 1/00 | (2006.01) | |
| H04N 5/232 | (2006.01) | |
| A61B 34/10 | (2016.01) | |
| A61B 90/00 | (2016.01) | |

(52) U.S. Cl.
CPC .......... *A61B 5/0059* (2013.01); *A61B 5/0077* (2013.01); *A61B 5/01* (2013.01); *A61B 5/1073* (2013.01); *A61B 5/1077* (2013.01); *A61B 5/1079* (2013.01); *A61B 5/14539* (2013.01); *A61B 5/444* (2013.01); *A61B 5/447* (2013.01); *A61B 5/6898* (2013.01); *A61B 5/7275* (2013.01); *A61B 5/7282* (2013.01); *A61B 5/743* (2013.01); *A61B 5/746* (2013.01); *A61B 5/748* (2013.01); *A61B 5/7485* (2013.01); *A61B 8/488* (2013.01); *A61B 8/5223* (2013.01); *G01B 11/002* (2013.01); *G01B 11/02* (2013.01); *G01B 11/14* (2013.01); *G01B 11/22* (2013.01); *G01B 11/285* (2013.01); *G06T 7/0004* (2013.01); *G06T 7/0014* (2013.01); *H04N 1/00209* (2013.01); *H04N 1/00244* (2013.01); *H04N 5/23222* (2013.01); *H04N 5/23293* (2013.01); *A61B 2034/105* (2016.02); *A61B 2090/367* (2016.02); *A61B 2576/02* (2013.01); *G06T 2207/10028* (2013.01); *G06T 2207/30088* (2013.01)

(56) References Cited

U.S. PATENT DOCUMENTS

| | | | |
|---|---|---|---|
| 4,090,501 | A | 5/1978 | Chaitin |
| 4,170,987 | A | 10/1979 | Anselmo et al. |
| 4,236,082 | A | 11/1980 | Butler |
| 4,505,583 | A | 3/1985 | Konomi |
| 4,515,165 | A | 5/1985 | Carroll |
| 4,535,782 | A | 8/1985 | Zoltan |
| 4,556,057 | A | 12/1985 | Hiruma et al. |
| 4,724,480 | A | 2/1988 | Hecker et al. |
| 4,736,739 | A | 4/1988 | Flaton |
| 4,768,513 | A | 9/1988 | Suzuki |
| 4,773,097 | A | 9/1988 | Suzaki et al. |
| 4,821,117 | A | 4/1989 | Sekiguchi |
| 4,839,807 | A | 6/1989 | Doi et al. |
| 4,851,984 | A | 7/1989 | Doi et al. |
| 4,894,547 | A | 1/1990 | Leffell et al. |
| 4,930,516 | A | 6/1990 | Alfano et al. |
| 4,957,114 | A | 9/1990 | Zeng et al. |
| 4,979,815 | A | 12/1990 | Tsikos |
| 4,996,994 | A | 3/1991 | Steinhauer et al. |
| D315,901 | S | 4/1991 | Knowles |
| 5,003,977 | A | 4/1991 | Suzuki et al. |
| 5,016,173 | A | 5/1991 | Kenet et al. |
| 5,036,853 | A | 8/1991 | Jeffcoat et al. |
| 5,080,100 | A | 1/1992 | Trotel |
| 5,157,461 | A | 10/1992 | Page |
| 5,174,297 | A | 12/1992 | Daikuzono |
| 5,241,468 | A | 8/1993 | Kenet |
| 5,270,168 | A | 12/1993 | Grinnell |
| 5,319,550 | A | 6/1994 | Griffith |
| 5,363,854 | A | 11/1994 | Martens et al. |
| 5,369,496 | A | 11/1994 | Alfano et al. |
| 5,396,331 | A | 3/1995 | Kitoh et al. |
| 5,408,996 | A | 4/1995 | Salb |
| 5,421,337 | A | 6/1995 | Richards-Kortum et al. |
| 5,515,449 | A | 5/1996 | Tsuruoka et al. |
| 5,519,208 | A | 5/1996 | Esparza et al. |
| 5,528,703 | A | 6/1996 | Lee |
| 5,531,520 | A | 7/1996 | Grimson et al. |
| 5,532,824 | A | 7/1996 | Harvey et al. |
| 5,561,526 | A | 10/1996 | Huber et al. |
| 5,588,428 | A * | 12/1996 | Smith .................. A61B 5/1077 382/128 |
| 5,590,660 | A | 1/1997 | MacAulay et al. |
| 5,603,318 | A | 2/1997 | Heilbrun et al. |
| 5,627,907 | A | 5/1997 | Gur et al. |
| 5,644,141 | A | 7/1997 | Hooker et al. |
| 5,648,915 | A | 7/1997 | McKinney et al. |
| 5,673,300 | A | 9/1997 | Reckwerdt et al. |
| 5,689,575 | A | 11/1997 | Sako et al. |
| 5,699,798 | A | 12/1997 | Hochman et al. |
| 5,701,902 | A | 12/1997 | Vari et al. |
| 5,717,791 | A | 2/1998 | Labaere et al. |
| D393,068 | S | 3/1998 | Kodama |
| 5,740,268 | A | 4/1998 | Nishikawa et al. |
| 5,749,830 | A | 5/1998 | Kaneko et al. |
| 5,784,162 | A | 7/1998 | Cabib et al. |
| 5,791,346 | A | 8/1998 | Craine et al. |
| 5,799,100 | A | 8/1998 | Clarke et al. |
| 5,810,014 | A | 9/1998 | Davis et al. |
| 5,836,872 | A | 11/1998 | Kenet et al. |
| 5,910,972 | A | 6/1999 | Ohkubo et al. |
| 5,921,937 | A | 7/1999 | Davis et al. |
| 5,946,645 | A | 8/1999 | Rioux et al. |
| 5,957,837 | A | 9/1999 | Raab |
| 5,967,797 | A | 10/1999 | Maldonado |
| 5,967,979 | A | 10/1999 | Taylor et al. |
| 5,969,822 | A | 10/1999 | Fright et al. |
| 5,974,165 | A | 10/1999 | Giger et al. |
| 6,032,070 | A | 2/2000 | Flock et al. |
| 6,081,612 | A | 6/2000 | Gutkowicz-Krusin et al. |
| 6,081,739 | A | 6/2000 | Lemchen |
| 6,091,995 | A | 7/2000 | Ingle et al. |
| 6,101,408 | A | 8/2000 | Craine et al. |
| 6,208,749 | B1 | 3/2001 | Gutkowicz-Krusin et al. |
| 6,215,893 | B1 | 4/2001 | Leshem et al. |
| 6,265,151 | B1 | 7/2001 | Canter et al. |
| 6,266,453 | B1 | 7/2001 | Hibbard et al. |
| 6,272,278 | B1 | 8/2001 | Takahata et al. |
| 6,278,793 | B1 | 8/2001 | Gur et al. |
| 6,307,957 | B1 | 10/2001 | Gutkowicz-Krusin et al. |
| 6,324,417 | B1 | 11/2001 | Cotton |
| D453,350 | S | 2/2002 | Fenton |
| 6,359,513 | B1 | 3/2002 | Kuo et al. |
| 6,359,612 | B1 | 3/2002 | Peter |
| D455,166 | S | 4/2002 | Raad |
| 6,381,026 | B1 | 4/2002 | Schiff et al. |
| 6,381,488 | B1 | 4/2002 | Dickey et al. |
| 6,392,744 | B1 | 5/2002 | Holec |
| 6,396,270 | B1 | 5/2002 | Smith |
| 6,413,212 | B1 | 7/2002 | Raab |
| 6,421,463 | B1 | 7/2002 | Poggio et al. |
| 6,427,022 | B1 | 7/2002 | Craine et al. |
| 6,491,632 | B1 | 12/2002 | Taylor |
| 6,567,682 | B1 | 5/2003 | Osterweil et al. |
| 6,594,388 | B1 | 7/2003 | Gindele et al. |
| 6,594,516 | B1 | 7/2003 | Steckner et al. |
| 6,603,552 | B1 | 8/2003 | Cline et al. |
| 6,611,617 | B1 | 8/2003 | Crampton |
| 6,611,833 | B1 | 8/2003 | Johnson |

(56) References Cited

U.S. PATENT DOCUMENTS

| | | |
|---|---|---|
| 6,631,286 B2 | 10/2003 | Pfeiffer et al. |
| 6,648,820 B1 | 11/2003 | Sarel |
| 6,671,349 B1 | 12/2003 | Griffith |
| 6,678,001 B1 | 1/2004 | Elberbaum |
| 6,690,964 B2 | 2/2004 | Bieger et al. |
| 6,715,675 B1 | 4/2004 | Rosenfeld |
| 6,754,370 B1 | 6/2004 | Hall-Holt et al. |
| 6,770,186 B2 | 8/2004 | Rosenfeld et al. |
| 6,798,571 B2 | 9/2004 | Wetzel et al. |
| 6,809,803 B1 | 10/2004 | O'Brien et al. |
| 6,810,279 B2 | 10/2004 | Mansfield et al. |
| 6,816,606 B2 | 11/2004 | Wetzel et al. |
| 6,816,847 B1 | 11/2004 | Toyama |
| 6,862,410 B2 | 3/2005 | Miyoshi |
| 6,862,542 B2 | 3/2005 | Lockhart et al. |
| 6,873,340 B2 | 3/2005 | Luby |
| 6,873,716 B2 | 3/2005 | Bowker |
| 6,879,394 B2 | 4/2005 | Amblard et al. |
| 6,907,193 B2 | 6/2005 | Kollias et al. |
| 6,915,073 B2 | 7/2005 | Seo |
| 6,922,523 B2 | 7/2005 | Merola et al. |
| 6,941,323 B1 | 9/2005 | Galperin |
| 6,961,517 B2 | 11/2005 | Merola et al. |
| 6,968,094 B1 | 11/2005 | Gallagher |
| 6,993,169 B2 | 1/2006 | Wetzel et al. |
| 7,006,223 B2 | 2/2006 | Mullani |
| 7,013,172 B2 | 3/2006 | Mansfield et al. |
| 7,015,906 B2 | 3/2006 | Olschewski et al. |
| 7,027,153 B2 | 4/2006 | Mullani |
| 7,040,536 B2 | 5/2006 | Rosenfeld |
| 7,054,674 B2 | 5/2006 | Cane et al. |
| 7,064,311 B2 | 6/2006 | Jung et al. |
| 7,068,828 B2 | 6/2006 | Kim et al. |
| 7,068,836 B1 | 6/2006 | Rubbert et al. |
| 7,074,509 B2 | 7/2006 | Rosenfeld et al. |
| 7,103,205 B2 | 9/2006 | Wang et al. |
| 7,106,885 B2 | 9/2006 | Osterweil et al. |
| 7,127,094 B1 | 10/2006 | Elbaum et al. |
| 7,127,280 B2 | 10/2006 | Dauga |
| 7,128,894 B1 | 10/2006 | Tannous et al. |
| 7,130,465 B2 | 10/2006 | Muenzenmayer et al. |
| 7,136,191 B2 | 11/2006 | Kaltenbach et al. |
| D533,555 S | 12/2006 | Odhe et al. |
| 7,155,049 B2 | 12/2006 | Wetzel et al. |
| 7,162,063 B1 | 1/2007 | Craine et al. |
| 7,167,243 B2 | 1/2007 | Mullani |
| 7,167,244 B2 | 1/2007 | Mullani |
| 7,181,363 B2 | 2/2007 | Ratti et al. |
| 7,194,114 B2 | 3/2007 | Schneiderman |
| 7,212,660 B2 | 5/2007 | Wetzel et al. |
| 7,227,621 B2 | 6/2007 | Lee et al. |
| 7,233,693 B2 | 6/2007 | Momma |
| D547,347 S | 7/2007 | Kim |
| 7,248,724 B2 * | 7/2007 | Gutenev ............... A61B 5/445 382/128 |
| D554,682 S | 11/2007 | Martinez |
| 7,295,226 B1 | 11/2007 | Meron et al. |
| 7,298,881 B2 | 11/2007 | Giger et al. |
| D561,804 S | 2/2008 | Asai |
| 7,347,365 B2 | 3/2008 | Rowe |
| 7,376,346 B2 | 5/2008 | Merola et al. |
| 7,400,754 B2 | 7/2008 | Jung et al. |
| 7,421,102 B2 | 9/2008 | Wetzel et al. |
| 7,426,319 B2 | 9/2008 | Takahashi |
| 7,440,597 B2 | 10/2008 | Rowe |
| 7,450,783 B2 | 11/2008 | Talapov et al. |
| 7,460,250 B2 | 12/2008 | Keightley et al. |
| 7,474,415 B2 | 1/2009 | Lin et al. |
| 7,487,063 B2 | 2/2009 | Tubic et al. |
| 7,489,799 B2 | 2/2009 | Nilsen et al. |
| 7,495,208 B2 | 2/2009 | Czarnek et al. |
| 7,496,399 B2 | 2/2009 | Maschke |
| 7,509,861 B2 | 3/2009 | Masotti et al. |
| 7,538,869 B2 | 5/2009 | Treado et al. |
| 7,545,963 B2 | 6/2009 | Rowe |
| D597,205 S | 7/2009 | Koch |
| 7,580,590 B2 | 8/2009 | Lin et al. |
| 7,581,191 B2 | 8/2009 | Rice et al. |
| 7,587,618 B2 | 9/2009 | Inui et al. |
| 7,595,878 B2 | 9/2009 | Nelson et al. |
| D603,441 S | 11/2009 | Wada |
| 7,613,335 B2 | 11/2009 | McLennan et al. |
| 7,620,211 B2 | 11/2009 | Browne et al. |
| 7,647,085 B2 | 1/2010 | Cane et al. |
| 7,668,350 B2 | 2/2010 | Rowe |
| 7,684,589 B2 | 3/2010 | Nilsen et al. |
| 7,724,379 B2 | 5/2010 | Kawasaki et al. |
| 7,729,747 B2 | 6/2010 | Stranc et al. |
| 7,735,729 B2 | 6/2010 | Rowe |
| 7,738,032 B2 | 6/2010 | Kollias et al. |
| 7,751,594 B2 | 7/2010 | Rowe et al. |
| 7,765,487 B2 | 7/2010 | Cable |
| 7,819,311 B2 | 10/2010 | Rowe et al. |
| 7,869,641 B2 | 1/2011 | Wetzel et al. |
| 7,876,948 B2 | 1/2011 | Wetzel et al. |
| 7,881,777 B2 | 2/2011 | Docherty et al. |
| 7,894,645 B2 | 2/2011 | Barsky |
| 7,912,320 B1 | 3/2011 | Minor |
| 7,912,534 B2 | 3/2011 | Grinvald et al. |
| 7,916,834 B2 | 3/2011 | Piorek et al. |
| 7,931,149 B2 | 4/2011 | Gilad et al. |
| 8,000,776 B2 | 8/2011 | Gono |
| 8,019,801 B1 | 9/2011 | Robb et al. |
| 8,026,942 B2 | 9/2011 | Payonk et al. |
| 8,071,242 B2 | 12/2011 | Rosenfeld et al. |
| 8,078,262 B2 | 12/2011 | Murphy et al. |
| 8,094,294 B2 | 1/2012 | Treado et al. |
| 8,105,233 B2 | 1/2012 | Abou El Kheir |
| D653,687 S | 2/2012 | Yu |
| 8,123,704 B2 | 2/2012 | Richards |
| 8,150,500 B2 | 4/2012 | Goldman et al. |
| 8,161,826 B1 | 4/2012 | Taylor |
| 8,165,357 B2 | 4/2012 | Rowe |
| 8,184,873 B2 | 5/2012 | Rowe et al. |
| D662,122 S | 6/2012 | Goodwin |
| 8,213,695 B2 | 7/2012 | Zouridakis |
| 8,218,873 B2 | 7/2012 | Boncyk et al. |
| 8,218,874 B2 | 7/2012 | Boncyk et al. |
| 8,224,077 B2 | 7/2012 | Boncyk et al. |
| 8,224,078 B2 | 7/2012 | Boncyk et al. |
| 8,224,079 B2 | 7/2012 | Boncyk et al. |
| 8,229,185 B2 | 7/2012 | Ennis et al. |
| 8,238,623 B2 | 8/2012 | Stephan et al. |
| 8,306,334 B2 | 11/2012 | Paschalakis et al. |
| 8,326,031 B2 | 12/2012 | Boncyk et al. |
| 8,335,351 B2 | 12/2012 | Boncyk et al. |
| 8,437,544 B2 | 5/2013 | Boncyk et al. |
| 8,457,395 B2 | 6/2013 | Boncyk et al. |
| 8,463,030 B2 | 6/2013 | Boncyk et al. |
| 8,463,031 B2 | 6/2013 | Boncyk et al. |
| 8,467,600 B2 | 6/2013 | Boncyk et al. |
| 8,467,602 B2 | 6/2013 | Boncyk et al. |
| 8,478,036 B2 | 7/2013 | Boncyk et al. |
| 8,478,037 B2 | 7/2013 | Boncyk et al. |
| 8,480,641 B2 | 7/2013 | Jacobs |
| 8,488,880 B2 | 7/2013 | Boncyk et al. |
| 8,494,264 B2 | 7/2013 | Boncyk et al. |
| 8,520,942 B2 | 8/2013 | Boncyk et al. |
| 8,533,879 B1 | 9/2013 | Taylor |
| 8,548,245 B2 | 10/2013 | Boncyk et al. |
| 8,548,278 B2 | 10/2013 | Boncyk et al. |
| 8,582,817 B2 | 11/2013 | Boncyk et al. |
| 8,588,476 B1 | 11/2013 | Spicola, Jr. |
| 8,588,527 B2 | 11/2013 | Boncyk et al. |
| D697,210 S | 1/2014 | Delaney et al. |
| 8,638,986 B2 | 1/2014 | Jiang et al. |
| 8,661,915 B2 | 3/2014 | Taylor |
| 8,712,193 B2 | 4/2014 | Boncyk et al. |
| 8,718,410 B2 | 5/2014 | Boncyk et al. |
| 8,734,342 B2 | 5/2014 | Cable |
| 8,755,053 B2 | 6/2014 | Fright et al. |
| 8,768,052 B2 | 7/2014 | Kawano |
| 8,774,463 B2 | 7/2014 | Boncyk et al. |
| 8,787,621 B2 | 7/2014 | Spicola, Sr. et al. |

(56) References Cited

U.S. PATENT DOCUMENTS

| | | | |
|---|---|---|---|
| 8,787,630 B2 | 7/2014 | Rowe | |
| 8,795,169 B2 | 8/2014 | Cosentino et al. | |
| 8,798,368 B2 | 8/2014 | Boncyk et al. | |
| 8,800,386 B2 | 8/2014 | Taylor | |
| 8,814,841 B2 | 8/2014 | Hartwell | |
| 8,824,738 B2 | 9/2014 | Boncyk et al. | |
| 8,837,868 B2 | 9/2014 | Boncyk et al. | |
| 8,842,941 B2 | 9/2014 | Boncyk et al. | |
| D714,940 S | 10/2014 | Kim | |
| 8,855,423 B2 | 10/2014 | Boncyk et al. | |
| 8,861,859 B2 | 10/2014 | Boncyk et al. | |
| 8,867,839 B2 | 10/2014 | Boncyk et al. | |
| 8,873,891 B2 | 10/2014 | Boncyk et al. | |
| 8,875,331 B2 | 11/2014 | Taylor | |
| 8,885,983 B2 | 11/2014 | Boncyk et al. | |
| 8,892,190 B2 | 11/2014 | Docherty et al. | |
| 8,904,876 B2 | 12/2014 | Taylor et al. | |
| 8,913,800 B2 | 12/2014 | Rowe | |
| 8,923,563 B2 | 12/2014 | Boncyk et al. | |
| 8,938,096 B2 | 1/2015 | Boncyk et al. | |
| 8,939,918 B2 | 1/2015 | Richards | |
| 8,948,459 B2 | 2/2015 | Boncyk et al. | |
| 8,948,460 B2 | 2/2015 | Boncyk et al. | |
| D724,216 S | 3/2015 | Gant et al. | |
| 8,997,588 B2 | 4/2015 | Taylor | |
| 9,014,513 B2 | 4/2015 | Boncyk et al. | |
| 9,014,514 B2 | 4/2015 | Boncyk et al. | |
| 9,014,515 B2 | 4/2015 | Boncyk, V et al. | |
| 9,020,305 B2 | 4/2015 | Boncyk et al. | |
| 9,025,813 B2 | 5/2015 | Boncyk et al. | |
| 9,025,814 B2 | 5/2015 | Boncyk et al. | |
| 9,031,278 B2 | 5/2015 | Boncyk et al. | |
| 9,036,947 B2 | 5/2015 | Boncyk et al. | |
| 9,036,948 B2 | 5/2015 | Boncyk et al. | |
| 9,041,810 B2 | 5/2015 | Ecker et al. | |
| 9,110,925 B2 | 8/2015 | Boncyk et al. | |
| 9,116,920 B2 | 8/2015 | Boncyk et al. | |
| 9,135,355 B2 | 9/2015 | Boncyk et al. | |
| 9,141,714 B2 | 9/2015 | Boncyk et al. | |
| 9,148,562 B2 | 9/2015 | Boncyk et al. | |
| D740,945 S | 10/2015 | Booth | |
| 9,154,694 B2 | 10/2015 | Boncyk et al. | |
| 9,154,695 B2 | 10/2015 | Boncyk et al. | |
| 9,167,800 B2 | 10/2015 | Spicola, Jr. | |
| 9,179,844 B2 | 11/2015 | Fright et al. | |
| 9,186,053 B2 | 11/2015 | Viola | |
| 9,224,205 B2 | 12/2015 | Tsin et al. | |
| 9,235,600 B2 | 1/2016 | Boncyk et al. | |
| 9,244,943 B2 | 1/2016 | Boncyk et al. | |
| 9,262,440 B2 | 2/2016 | Boncyk et al. | |
| 9,288,271 B2 | 3/2016 | Boncyk et al. | |
| 9,311,540 B2 | 4/2016 | Ecker et al. | |
| 9,311,552 B2 | 4/2016 | Boncyk et al. | |
| 9,311,553 B2 | 4/2016 | Boncyk et al. | |
| 9,311,554 B2 | 4/2016 | Boncyk et al. | |
| 9,317,769 B2 | 4/2016 | Boncyk et al. | |
| 9,324,004 B2 | 4/2016 | Boncyk et al. | |
| 9,330,326 B2 | 5/2016 | Boncyk et al. | |
| 9,330,327 B2 | 5/2016 | Boncyk et al. | |
| 9,330,328 B2 | 5/2016 | Boncyk et al. | |
| 9,330,453 B2 | 5/2016 | Soldatitsch et al. | |
| 9,342,748 B2 | 5/2016 | Boncyk et al. | |
| 9,377,295 B2 | 6/2016 | Fright et al. | |
| 9,395,234 B2 | 7/2016 | Cosentino et al. | |
| 9,399,676 B2 | 7/2016 | Schurpf et al. | |
| 9,438,775 B2 | 9/2016 | Powers | |
| 9,451,928 B2 | 9/2016 | Falco et al. | |
| 9,861,285 B2 | 1/2018 | Fright et al. | |
| 9,955,910 B2 | 5/2018 | Fright et al. | |
| 10,013,527 B2 | 7/2018 | Fairbairn et al. | |
| 2002/0054297 A1 | 5/2002 | Lee et al. | |
| 2002/0149585 A1 | 10/2002 | Kacyra et al. | |
| 2002/0197600 A1 | 12/2002 | Maione et al. | |
| 2003/0004405 A1 | 1/2003 | Townsend et al. | |
| 2003/0006770 A1 | 1/2003 | Smith | |
| 2003/0031383 A1 | 2/2003 | Gooch | |
| 2003/0036751 A1 | 2/2003 | Anderson et al. | |
| 2003/0085908 A1 | 5/2003 | Luby | |
| 2003/0164841 A1 | 9/2003 | Myers | |
| 2003/0164875 A1 | 9/2003 | Myers | |
| 2003/0229514 A2 | 12/2003 | Brown | |
| 2003/0231793 A1 | 12/2003 | Crampton | |
| 2004/0014165 A1 | 1/2004 | Keidar et al. | |
| 2004/0059199 A1* | 3/2004 | Thomas | A61B 5/445 600/300 |
| 2004/0080497 A1 | 4/2004 | Enmei | |
| 2004/0117343 A1 | 6/2004 | Johnson | |
| 2004/0136579 A1 | 7/2004 | Gutenev | |
| 2004/0146290 A1 | 7/2004 | Kollias et al. | |
| 2004/0201694 A1 | 10/2004 | Gartstein et al. | |
| 2004/0225222 A1 | 11/2004 | Zeng et al. | |
| 2004/0264749 A1 | 12/2004 | Skladnev et al. | |
| 2005/0012817 A1 | 1/2005 | Hampapur et al. | |
| 2005/0027567 A1 | 2/2005 | Taha | |
| 2005/0033142 A1 | 2/2005 | Madden et al. | |
| 2005/0084176 A1 | 4/2005 | Talapov et al. | |
| 2005/0094262 A1 | 5/2005 | Spediacci et al. | |
| 2005/0111757 A1 | 5/2005 | Brackett et al. | |
| 2005/0154276 A1 | 7/2005 | Barducci et al. | |
| 2005/0190988 A1 | 9/2005 | Feron | |
| 2005/0237384 A1 | 10/2005 | Jess et al. | |
| 2005/0259281 A1 | 11/2005 | Boust | |
| 2005/0273011 A1 | 12/2005 | Hattery et al. | |
| 2005/0273267 A1 | 12/2005 | Maione | |
| 2006/0008178 A1 | 1/2006 | Seeger et al. | |
| 2006/0012802 A1 | 1/2006 | Shirley | |
| 2006/0036135 A1 | 2/2006 | Kern | |
| 2006/0036156 A1 | 2/2006 | Lachaine et al. | |
| 2006/0044546 A1 | 3/2006 | Lewin et al. | |
| 2006/0055943 A1 | 3/2006 | Kawasaki et al. | |
| 2006/0058665 A1 | 3/2006 | Chapman | |
| 2006/0072122 A1 | 4/2006 | Hu et al. | |
| 2006/0073132 A1 | 4/2006 | Congote | |
| 2006/0089553 A1 | 4/2006 | Cotton | |
| 2006/0098876 A1 | 5/2006 | Buscema | |
| 2006/0135953 A1 | 6/2006 | Kania et al. | |
| 2006/0151601 A1 | 7/2006 | Rosenfeld | |
| 2006/0204072 A1 | 9/2006 | Wetzel et al. | |
| 2006/0210132 A1 | 9/2006 | Christiansen et al. | |
| 2006/0222263 A1 | 10/2006 | Carlson | |
| 2006/0268148 A1 | 11/2006 | Kollias et al. | |
| 2006/0269125 A1 | 11/2006 | Kalevo et al. | |
| 2006/0293613 A1 | 12/2006 | Fatehi et al. | |
| 2007/0065009 A1 | 3/2007 | Ni et al. | |
| 2007/0097381 A1 | 5/2007 | Tobiason et al. | |
| 2007/0125390 A1 | 6/2007 | Afriat et al. | |
| 2007/0129602 A1 | 6/2007 | Bettesh et al. | |
| 2007/0229850 A1 | 10/2007 | Herber | |
| 2007/0273894 A1 | 11/2007 | Johnson | |
| 2007/0276195 A1 | 11/2007 | Xu et al. | |
| 2007/0276309 A1 | 11/2007 | Xu et al. | |
| 2007/0295888 A1* | 12/2007 | Czarnek | A61B 5/445 250/206 |
| 2008/0006282 A1 | 1/2008 | Sukovic | |
| 2008/0021329 A1 | 1/2008 | Wood et al. | |
| 2008/0045807 A1 | 2/2008 | Psota et al. | |
| 2008/0088704 A1 | 4/2008 | Wendelken et al. | |
| 2008/0098322 A1 | 4/2008 | Champion et al. | |
| 2008/0126478 A1 | 5/2008 | Ferguson et al. | |
| 2008/0165357 A1 | 7/2008 | Stem | |
| 2008/0232679 A1 | 9/2008 | Hahn | |
| 2008/0246759 A1 | 10/2008 | Summers | |
| 2008/0275315 A1 | 11/2008 | Oka et al. | |
| 2008/0285056 A1 | 11/2008 | Blayvas | |
| 2008/0312642 A1 | 12/2008 | Kania et al. | |
| 2008/0312643 A1 | 12/2008 | Kania et al. | |
| 2009/0116712 A1 | 5/2009 | Al-Moosawi et al. | |
| 2009/0118720 A1 | 5/2009 | Black et al. | |
| 2009/0213213 A1 | 8/2009 | Fright et al. | |
| 2009/0221874 A1 | 9/2009 | Vinther | |
| 2009/0225333 A1 | 9/2009 | Bendall | |
| 2009/0234313 A1 | 9/2009 | Mullejans et al. | |
| 2010/0004564 A1 | 1/2010 | Jendle | |
| 2010/0020164 A1 | 1/2010 | Perrault | |

(56) References Cited

U.S. PATENT DOCUMENTS

| | | | |
|---|---|---|---|
| 2010/0091104 A1 | 4/2010 | Sprigle et al. | |
| 2010/0111387 A1 | 5/2010 | Christiansen, II et al. | |
| 2010/0121201 A1 | 5/2010 | Papaionnou | |
| 2010/0149551 A1 | 6/2010 | Malinkevich | |
| 2010/0156921 A1 | 6/2010 | McLennan et al. | |
| 2010/0191126 A1 | 7/2010 | Al-Moosawi et al. | |
| 2010/0278312 A1 | 11/2010 | Ortiz | |
| 2011/0125028 A1 | 5/2011 | Wood et al. | |
| 2011/0190637 A1 | 8/2011 | Knobel et al. | |
| 2012/0035469 A1 | 2/2012 | Whelan et al. | |
| 2012/0059266 A1 | 3/2012 | Davis et al. | |
| 2012/0078088 A1 | 3/2012 | Whitestone et al. | |
| 2012/0078113 A1 | 3/2012 | Whitestone et al. | |
| 2012/0253200 A1 | 10/2012 | Stolka et al. | |
| 2012/0265236 A1 | 10/2012 | Wesselmann | |
| 2012/0275668 A1 | 11/2012 | Chou et al. | |
| 2013/0051651 A1 | 2/2013 | Leary et al. | |
| 2013/0137991 A1* | 5/2013 | Fright | A61B 5/0013 600/476 |
| 2013/0335545 A1 | 12/2013 | Darling | |
| 2014/0048687 A1 | 2/2014 | Drzymala et al. | |
| 2014/0088402 A1 | 3/2014 | Xu | |
| 2014/0354830 A1 | 12/2014 | Schafer et al. | |
| 2015/0089994 A1 | 4/2015 | Richards | |
| 2015/0142462 A1 | 5/2015 | Vaidya et al. | |
| 2015/0150457 A1 | 6/2015 | Wu et al. | |
| 2015/0214993 A1 | 7/2015 | Huang | |
| 2015/0250416 A1 | 9/2015 | LaPlante et al. | |
| 2015/0265236 A1 | 9/2015 | Garner et al. | |
| 2015/0270734 A1 | 9/2015 | Davison et al. | |
| 2016/0157725 A1 | 6/2016 | Munoz | |
| 2016/0206205 A1 | 7/2016 | Wu et al. | |
| 2016/0259992 A1 | 9/2016 | Knodt et al. | |
| 2016/0261133 A1 | 9/2016 | Wang | |
| 2016/0262659 A1 | 9/2016 | Fright et al. | |
| 2016/0284084 A1 | 9/2016 | Gurcan et al. | |
| 2016/0338594 A1 | 11/2016 | Spahn et al. | |
| 2017/0079577 A1 | 3/2017 | Fright et al. | |
| 2017/0084024 A1 | 3/2017 | Gurevich | |
| 2017/0086940 A1 | 3/2017 | Nakamura | |
| 2017/0127196 A1 | 5/2017 | Blum et al. | |
| 2018/0132726 A1 | 5/2018 | Dickie et al. | |
| 2018/0254100 A1 | 9/2018 | Fairbairn et al. | |
| 2018/0271378 A1 | 9/2018 | Fright et al. | |
| 2019/0273890 A1* | 9/2019 | Christiansen, II | A61B 5/445 |

FOREIGN PATENT DOCUMENTS

| | | | |
|---|---|---|---|
| DE | 4120074 | 1/1992 | |
| EP | 119660 | 9/1984 | |
| EP | 355221 | 2/1990 | |
| EP | 552526 | 7/1993 | |
| EP | 650694 | 5/1995 | |
| EP | 1210906 | 6/2002 | |
| EP | 1248237 A2 | 10/2002 | |
| EP | 1351036 | 10/2003 | |
| EP | 1584405 | 10/2005 | |
| EP | 1611543 | 1/2006 | |
| EP | 1946567 | 7/2008 | |
| FR | 2570206 | 3/1986 | |
| NZ | 293713 | 9/1997 | |
| WO | 2000003210 | 1/2000 | |
| WO | 2000030337 | 5/2000 | |
| WO | WO-0030337 A2 * | 5/2000 | H04N 13/221 |
| WO | 2002065069 | 6/2002 | |
| WO | 2002001143 | 7/2002 | |
| WO | 2002093450 | 11/2002 | |
| WO | 2004092874 | 10/2004 | |
| WO | 2004095372 | 11/2004 | |
| WO | 2005033620 | 4/2005 | |
| WO | 2006078902 A2 | 7/2006 | |
| WO | 2007029038 A1 | 3/2007 | |
| WO | 2007043899 A1 | 4/2007 | |
| WO | 2007059780 A1 | 5/2007 | |
| WO | 2008033010 A1 | 3/2008 | |
| WO | 2008039539 A2 | 4/2008 | |
| WO | 2008048424 A2 | 4/2008 | |
| WO | 2008057056 A1 | 5/2008 | |
| WO | 2008071414 A1 | 6/2008 | |
| WO | 2008080385 A1 | 7/2008 | |
| WO | 2009046218 A2 | 4/2009 | |
| WO | 2010048960 A1 | 5/2010 | |
| WO | 2012146720 | 11/2012 | |
| WO | 2016199134 A1 | 12/2016 | |
| WO | 2018185560 A2 | 10/2018 | |

OTHER PUBLICATIONS

Bolton, L., "Re Measuring Wound Length, Width, and Area: Which Technique?" Letters, Advances in Skin & Wound Care, pp. 450-452, vol. 21, No. 10.

Briers, J.D., "Laser speckle contrct imaging for measuring blood flow," Optica Applicata, 2007, pp. 139-152, vol. XXXVII, No. 1-2.

Cardinal et al., "Early healing rates and wound area measurements are reliable predictors of later complete wound closure," Wound Rep. Reg., 2008, pp. 19-22, vol. 16.

Cardinal et al., "Wound shape geometry measurements correlate to eventual wound healing," Wound Rep. Reg., 2009, pp. 173-178, vol. 17.

Cleator et al., "Mobile wound care: Transforming care through technology," Rehab & Community Care Medicine, Winter 2008, pp. 14-15.

De Vet, H C., et al., "When to use agreement versus reliability measures", J Clin Eoidemiol 59 (10), (Oct. 2006), 1033-9.

Duckworth et al., "A Clinically Affordable Non-Contact Wound Measurement Device," 2007, pp. 1-3.

Fette, A.M., "A clinimetric analysis of wound measurement tools," World Wide Wounds, 2006, [retrieved on Jul. 26, 2006]. Retrieved from the Internet: <URL: http://www.worldwidewounds.com/2006/January/Fette/Clinimetric-Ana . . . >, 6 pages.

Gethin et al., "Wound Measurement: the contribution to practice," EWMA Journal, 2007, pp. 26-28, vol. 7, No. 1.

Haghpanah et al., "Reliability of Electronic Versus Manual Wound Measurement Techniques," Arch Phys Med Rehabil, Oct. 2006, pp. 1396-1402, vol. 87.

HSA Global, "Mobile Wound Care", Marketing material (2009).

International Search Report and Written Opinion dated Jan. 23, 2019, International Application No. PCT/IB2018/000447, 20 pages.

International Search Report and Written Opinion dated Jul. 2, 2019, International Application No. PCT/IB2018/001572, 17 pages.

International Search Report and Written Opinion dated Mar. 1, 2007, International Application No. PCT/NZ2006/000262, 12 pages.

Kecelj-Leskovec et al., "Measurement of venous leg ulcers with a laser-based three-dimensional method: Comparison to computer planimetry with photography," Wound Rep Reg, 2007, pp. 767-771, vol. 15.

Khashram et al., "Effect of TNP on the microbiology of venous leg ulcers: a pilot study," J Wound Care, Apr. 2009, pp. 164-167, vol. 18, No. 4.

Korber et al., "Three-dimensional documentation of wound healing: First results of a new objective method for measurement," JDDG, Oct. 2006, (Band 4), pp. 848-854.

Lakovou, D. et al., "Integrated sensors for robotic laser welding," Proceedings of the Third International WLT—Conference on Lasres in Manufacturing, Jun. 2005, pp. 1-6.

Langemo et al., "Measuring Wound Length, Width, and Area: Which Technique?", Advances in Skin & Wound Care, Jan. 2008, pp. 42-45, vol. 21, No. I.

Liu et al., "Wound measurement by curvature maps: a feasibility study," Physiol. Meas., 2006, pp. 1107-1123, vol. 27.

Molnar et al., "Use of Standardized, Quantitative Digital Photography in a Multicenter Web-based Study," 2009, ePlasty, pp. 19-26, vol. 9.

Payne, C., "Cost benefit comparison of plaster casts and optical scans of the foot for the manufacture of foot orthoses," AJPM, 2007, pp. 29-31, vol. 41, No. 2.

(56) References Cited

OTHER PUBLICATIONS

Rogers et al., "Measuring Wounds: Which Stick to Use?", Podiatry Management, Aug. 2008, pp. 85-90.
Salcido, R., "Pressure Ulcers and Wound Care," Physical Medicine and Rehabilitation, eMedicine, 2006, [retrieved on]. Retrieved from the Internet: <URL: http://www.emedicine.com/pmr/topic 179. htrn>, 25 pages.
Shaw et al., "An Evaluation of Three Wound Measurement Techniques in Diabetic Foot Wounds," Diabetes Care, 2007, [retrieved on Mar. 30, 2008]. Retrieved from the Internet: <URL: http://care.diabetesjournals.org/cgi/content/full/30/ I 0/2641 ?ck=nck>, 5 pages.
Treuillet et al., "Three-Dimensional Assessment of Skin Wounds Using a Standard Digital Camera," IEEE Transactions on Medical Imaging, May 2009, pp. 752-762, vol. 28, No. 5.
Wang et al., "A comparison of digital planimetry and transparency tracing based methods for measuring diabetic cutaneous ulcer surface area," Zhongguo Xiu Fu Chong Jian Wai Ke Za Zhi, May 2008, pp. 563-566, vol. 22, No. 5, [retrieved on Sep. 15, 2009]. Retrieved from the Internet: <URL: http://www.ncbi.nlm.nih.gov/pu bmed/ I 8630436?ordinalpos= I &itool=E . . . >, I page.
Wendelken et al., "Key Insights on Mapping Wounds With Ultrasound," Podiatry Today, Jul. 2008, [retrieved on Jul. 14, 2008]. Retrieved from the Internet: <URL: http://www.podiatrytoday.com/article/5831>, 5 pages.
Afromowitz, et al., "Multispectral Imaging of Burn Wounds: A New Clinical Instrument for Evaluating Burn Depth", IEEE Transactions on Biomedical Engineering, vol. 35, No. 10, pp. 842-850; Oct. 1988.
Ahroni, JH et al "Reliability of computerized wound surface area determinations" Wounds: A Compendium of Clinical Research and Practice, No. 4, (1992) 133-137.
Anderson, R., et al. "The Optics of Human Skin", The Journal of Investigative Dermatology, vol. 77, No. 1, pp. 13-19; Jul. 1981.
Armstrong, DG et al "Diabetic foot ulcers: prevention, diagnosis and classification" Am Fam Physician Mar. 15, 1998; 57 (6) :1325-32, 1337-8.
Bale, S, Harding K, Leaper D. An Introduction to Wounds. Emap Healthcare Ltd 2000.
Beaumont, E et al "RN Technology Scorecard: Wound Care Science at the Crossroads" American Journal of Nursing Dec. 1998 98(12):16-18, 20-21.
Bergstrom, N, Bennett MA, Carlson CE. Treatment of Pressure Ulcers: Clinical Practice Guideline No. 15. Rockville, MD: U.S. Department of Health and Human Services. Public Health Service, Agency for Health Care Policy and Research 1994: 95-0652: [O].
Berriss 1997: Automatic Quantitative Analysis of Healing Skin Wounds using Colour Digital Image Processing: William Paul Berriss, Stephen John Sangwine [E].
Binder, et al., "Application of an artificial neural network in epiluminescence microscopy pattern analysis of pigmented skin lesions: a pilot study", British Journal of Dermatology 130; pp. 460-465; 1994.
Bland, JM et al "Measurement error and correlation coefficients" BMJ Jul. 6, 1996; 313 (7048) :41-2.
Bland, JM et al "Measurement error" BMJ Jun. 29, 1996; 312 (7047) :1654.
Bohannon Richard; Barbara A Pfaller Documentation of Wound Surface Area from Tracings of Wound Perimeters [E].
Bostock, et al, Toward a neural network based system for skin cancer diagnosis; IEEE Conference on Artificial neural Networks, ISBN: 0-85296-573-7, pp. 215-219, May 1993.
BPG2005: Assessment and Management of Foot Ulcers for People with Diabetes:Nursing Best Practice Guidelines, Toronto, Ontario [E], Mar. 2013.
Briggs Corporation: Managed care making photo documentation a wound care standard. Wound care solutions product catalog 1997.
Brown, G "Reporting outcomes for Stage IV pressure ulcer healing: a proposal" Adv Skin Wound Care (2000)13:277-83.
Callieri 2003: Callieri M, Cignoni P, Pingi P, Scopigno R. Derma: Monitoring the evolution of skin lesions with a 3D system, VMV 2003. 8th International Fall Workshop, Vision, Modeling, and Visualization 2003, Nov. 19-21, 2003, Munich, Germany [E].
Campana: XML-based synchronization of mobile medical devices [E], 2002, 2 Pages.
Cascinelli, N., et al. "Results obtained by using a computerized image analysis system designed as an aid to diagnosis of cutaneous melanoma", Melanoma Research, vol. 2, pp. 163-170, 1992.
Collins, C et al "The Role of Ultrasound in Lower Extremity Wound Management" International Journal of Lower Extremity Wounds (2002) 1: 229-235.
Daubechies, I., "The Wavelet Transform, Time-Frequency Localization and Signal Analysis", IEEE Trans Inform Theory, vol. 36, No. 5, pp. 961-1005; Sep. 1990.
De Vet, HC et al "Current challenges in clinimetrics" J Clin Epidemiol Dec. 2003; 56 (12) :1137-41.
Debray, M., Couturier P, Greuillet F, Hohn C, Banerjee S, Gavazzi G, Franco A. "A preliminary study of the feasibility of wound telecare for the elderly." Journal of Telemedicine & Telecare 2001: 7(6): 353-8. [A].
Duff, et al. (2003), Loftus Hills A, Morrell C 2000 Clinical. Guidelines for the management of venous leg ulcers: Implementation Guide. Royal College of Nursing; 2000: 001 (213): 1-48. [E].
Ercal, F., "Detection of Skin Tumor Boundaries in Color Images", IEEE Transactions of Medical Imaging, vol. 12, No. 3, pp. 624-627, Sep. 1993.
Ercal, F., et al. "Neural Network Diagnosis of Malignant Melanoma From Color Images", IEEE Transactions of Biomedical Engineering, vol. 41, No. 9, pp. 837-845, Sep. 1994.
Ferrell, B "Pressure ulcers. Assessment of healing" Clin Geriatr Med (1997)13:575-87.
Fitzpatrick, R et al "Evaluating patient-based outcome measures for use in clinical trials" Health Technol Assess (1998); 2 (14) :i-iv, 1-74.
Flahr, et al. 2005: Clinimetrics and Wound Science [E].
Flanagan, M. "Improving accuracy of wound measurement in clinical practice" Ostomy Wound Manage Oct. 2003, 49(10):28-40.
Flanagan, M., "Wound measurement: can it help us to monitor progression to healing?" JWound Care May 2003, 12(5):189-94.
Gilman, T "Wound outcomes: the utility of surface measures" Int J Low Extrem Wounds Sep. 2004; 3 (3) :125-32.
Goldman, RJ "The patientcom, 1 year later" Adv Skin Wound Care Nov.-Dec. 2002; 15 (6) :254, 256.
Goldman, RJ et al "More than one way to measure a wound: An overview of tools and techniques" Adv Skin Wound Care (2002) 15:236-45.
Golston, et al. "Automatic Detection of Irregular Borders in Malanoma and Other Skin Tumors", Computerized Medical Imaging and Graphics, vol. 16, No. 3, pp. 199-203, 1992.
Graaf, R., et al. "Optical properties of human dermis in vitro and in vivo", Applied Optics, vol. 32, No. 4, pp. 435-447, Feb. 1, 1993.
Greene, A., "Computer image analysis in the diagnosis of melanoma", Journal of the American Academy of Dermatology; vol. 31, No. 6, pp. 958-964, 1994.
Griffin, JW et al "A comparison of photographic and transparency-based methods for measuring wound surface area" Phys Ther Feb. 1993; 73 (2) :117-22.
Hansen 1997: Wound Status Evaluation Using Color Image Processing Gary: L. Hansen, Ephraim M. Sparrow, Jaydeep Y. Kokate, Keith J. Leland, and Paul A. Iaizzo [E].
Hayes 2003:Hayes S, Dodds, S. Digital photography in wound care. Nursing Times 2003:9(42):48-9. [A].
Herbin, et al, Color Quantitation Through Image Processing in Dermatology; IEEE Transaction on Medical Imaging, vol. 9, Issue 3, pp. 262-269, Sep. 1990.
Hibbs, P "The economics of pressure ulcer prevention" Decubitus Aug. 1988; 1 (3) :32-8.
Houghton 2000: Houghton PE, Kincaid CB, Campbell KE, Woodbury MG, Keast DH. Photographic assessment of the appearance of chronic pressure and leg ulcers. Ostomy Wound management 2000: 46(4): 20-6, 28-30. [A].
Huang, C., et al."Border irregularity: atypical moles versus melanoma", Eur J Dermatol, vol. 6, pp. 270-273, Jun. 1996.

(56) References Cited

OTHER PUBLICATIONS

Iakovou, D. et al., "Integrated sensors for robotic laser welding," Proceedings of the Third International WLT—Conference on Lasers in Manufacturing, Jun. 2005, pp. 1-6.

International Search Report and Written Opinion for International Application No. PCT/US2004/028445 filed Sep. 1, 2004.

Johnson, JD (1995) Using ulcer surface area and volume to document wound size.

Jones, et al, An Instrument to Measure the Dimension of Skin Wounds; IEEE Transaction on Biomedical Engineering, ISSN: 0018-9294; vol. 42, Issue 5, pp. 464-470, May 1995.

Jones, TD "Improving the Precision of Leg Ulcer Area Measurement with Active Contour Models", PhD Thesis (1999) http://www.comp.glam.ac.uklpages/staff/tjones/ThesisOL/Title.Htm.

Jones, TD et al "An active contour model for measuring the area of leg ulcers" IEEE Trans Med Imaging Dec. 2000, 19(12):1202-10.

Kenet, R., et al. "Clinical Diagnosis of Pigmented Lesions Using Digital Epiluminescence Microscopy", Arch Dermatol, vol. 129, pp. 157-174; Feb. 1993.

Kloth, LC et al "A Randomized Controlled Clinical Trial to Evaluate the Effects of Noncontact Normothermic Wound Therapy on Chronic Full-thickness Pressure Ulcers" Advances in Skin & Wound Care Nov./Dec. 2002, 15(6):270-276.

Koren, et al, Interactive Wavelet Processing and Techniques Applied to Digital Mammography; IEEE Conference Proceedings, ISBN: 0-7803-3192-3; vol. 3, pp. 1415-1418, May 1996.

Kovesi, P., "Image Features From Phase Congruency", University of Western Australia, pp. 130; Technical Report 9/4, Revised Jun. 1995.

Krouskop, TA et al "A noncontact wound measurement system" J Rehabil Res Dev May-Jun. 2002, 39(3):337-45.

Kundin 1989: Kudin JI. A new way to size up a wound. American Journal of Nursing 1989: (2):206-7.

Langemo, DK et al "Comparison of 2 Wound Volume Measurement Methods" Advances in Skin & Wound Care Jul./Aug. 2001, vol. 14(4), 190-196.

Langemo, DK et al "Two- dimensional wound measurement: comparison of 4 techniques" Advances in Wound Care Nov.-Dec. 1998, 11(7):337-43.

Laughton, C et al "A comparison of four methods of obtaining a negative impression of the foot" J Am Podiatr Med Assoc May 2002; 92 (5) :261-8.

Lee, et al, A Multi-stage Segmentation Method for Images of Skin Lesions; IEEE Conference Proceedings on Communication, Computers, and Signal Processing, ISBN 0-7803-2553-2, pp. 602-605, May 1995.

Levoy, et al. "The Digital Michelangelo Project: 3D Scanning of Large Statues," ACM, 2000.

Lewis 1997: Lewis P, McCann R, Hidalgo P, Gorman M. Use of store and forward technology for vascular nursing teleconsultation service. Journal of Vascular Nursing 1997. 15(4): 116-23. [A].

Lewis, JS, Achilefu S, Garbow JR, Laforest R, Welch MJ., Small animal imaging. current technology and perspectives for oncological imaging, Radiation Sciences, Washington University School of Medicine, Saint Louis, MO, USA, Eur J Cancer. Nov. 2002;38(16):2173-88.

Li, D. 2004, Database design and implementation for wound measurement system. Biophotonics, 2004: 42-43. [E].

Lorimer, K "Continuity through best practice: design and implementation of a nurse-led community leg-ulcer service" Can J Nurs Res Jun. 2004, 36(2):105-12.

Lowery et al., "Technical Overview of a Web-based Telemedicine System for Wound Assessment," Advances in Skin & Wound Care, Jul./Aug. 2002, pp. 165-169, vol. 15, No. 4.

Lowson, S., "The safe practitioner: Getting the record straight: the need for accurate documentation," J Wound Care, Dec. 2004, vol. 13, No. 10, [retrieved on Dec. 17, 2004). Retrieved from the Internet: <URL: http://www.journalofwoundcare.com/nav?page=jowc.article&resource=I455125>, 2 pages.

Lucas, C., "Pressure ulcer surface area measurement using instant full-scale photography and transparency tracings," Advances in Skin & Wound Care, Jan./Feb. 2002, [retrieved on Jul. 28, 2006]. Retrieved from the Internet: <URL: http://www.findarticles.com/p/articles/mi_qa3977/is_200201 /ai_n904 . . . >, 7 pages.

Lunt, M.J., "Review of duplex and colour Doppler imaging of lower-limb arteries and veins," World Wide Wounds, 2000, [retrieved on Apr. 17, 2005]. Retrieved from the Internet: <URL: http://www.worldwidewounds.com/2000/sept/Michael-Lunt/Dopple . . . >, 6 pages.

Maglogiannis et al., "A system for the acquisition of reproducible digital skin lesions images," Technol and Health Care, 2003, pp. 425-441, vol. 11.

Malian et al., "MEDPHOS: A New Photogrammetric System for Medical Measurement," 2004, Commission V, WG V/3, 6 pages.

Mallat, S., et al. "Characterization of signals from multiscale edges", IEEE Trans Patt and Mech Int'l; 14:710-732; 1992.

Marchesini, R., et al. "In vivo Spectrophotometric Evaluation of Neoplastic and Non-Neoplastic Skin Pigmented Lesions. III. CCD Camera-Based Reflectance Imaging", Photochemistry and Photobiology, vol. 62, No. 1, pp. 151-154; 1995.

Marjanovic et al., "Measurement of the volume of a leg ulcer using a laser scanner," Physiol. Meas., 1998, pp. 535-543, vol. 19.

Mastronjcola et al., "Burn Depth Assessment Using a Tri-stimulus Colorimeter," Wounds—ISSN: !044-7946, Sep. 2005, pp. 255-258, vol. 17, No. 9.

McCardle, J., "Visitrak: wound measurement as an aid to making treatment decisions," The Diabetic Foot, Winter 2005, [retrieved on Mar. 30, 2008). Retrieved from the Internet: <URL: http://findarticles.com/p/articles/mi_ mOMDQ/is_ 4_8/ai_n16043804/print>, 4 pages.

Menzies, S., "The Morphologic Criteria of the Pseudopod in Surface Microscopy", Arch Dermatol, vol. 131, pp. 436-440, Apr. 1995.

Nachbar, et al., "The ABCD rule of dermatology", Journal of the American Academy of Dermatology, vol. 3, No. 4, pp. 551-559, Apr. 1994.

National Pressure Ulcer Advisory Panel, "FAQ: Photography for pressure ulcer documentation," 1 1P56, 4 pages.

National Pressure Ulcer Advisory Panel, Position Statement, 1998, [retrieved on Jan. 6, 2005). Retrieved from the Internet: <URL: http://www.npuap.org/>, 2 pages. (Pressure Ulcer Healing Chart attached, 2 pages).

Oduncu et al., "Analysis of Skin Wound Images Using Digital Color Image Processing: A Preliminary Communication," Lower Extremity Wounds, 2004, pp. 151-156, vol. 3, No. 3.

Pages, Jordi, et al., "Plane-to-plane positioning from image-based visual serving and structured light," Proceedings of 2004 IEEE/RSJ International Conference on Intelligent Robots and Systems, Sep. 28-Oct. 2, 2004, pp. 1004-1009.

Patete et al., "A non-invasive, three-dimensional, diagnostic laser imaging system for accurate wound analysis," Physiol. Meas., 1996, pp. 71-79, vol. 17.

Pehamberger, H., et al. "In vivo epiluminescence microscopy of pigmented skin lesions. I. Pattern analysis of pigmented skin lesions", Journal of American Academy of Dermatology, vol. 17, No. 4, pp. 571-583, Oct. 1987.

Plassman, et al. "Problems of Assessing Wound Size," Would healing Research Unit, University of Wales College of Medicine, Cardiff CF4 4XN, Wales, UK (1993) (Unpublished).

Plassmann et al., "MAVIS: A non-invasive instrument to measure area and volume of wounds," Medical Engineering & Physics, 1998, pp. 332-338, vol. 20.

Plassmann, P., "Recording Wounds—Documenting Woundcare," Medical Computing Group, 1998, pp. 1-31.

Romanelli et al., "Technological Advances in Wound Bed Measurements," Wounds, 2002, pp. 58-66, vol. 14, No. 2, [retrieved on Apr. 8, 2005]. Retrieved from the Internet: <URL: http:/lwww.medscape.com/viewarticle/430900 _print>, 8 pages.

Russell, L., "The importance of wound documentation & classification," British J Nursing, 1999, pp. 1342-1354, vol. 8, No. 20.

Salcido, R., "The Future of Wound Measurement," Advances in Skin & Wound Care, Mar./Apr. 2003, pp. 54, 56, vol. 13, No. 2.

Salmhofer, et al., "Wound teleconsultation in patients with chronic leg ulcers," 2005.

(56) References Cited

OTHER PUBLICATIONS

Sani-Kick et al., "Recording and Transmission of Digital Wound Images with the Help of a Mobile Device," 2002, 2 pages.

Santamaria et al., "The effectiveness of digital imaging and remote expert wound consultation on healing rates in chronic lower leg ulcers in the Kimberley region of Western Australia," Primary Intention, May 2004, pp. 62-70, vol. 12, No. 2.

Schindewolf, et al. "Comparison of classification rates for conventional and dermatoscopic images of malignant and benign melanocytic lesions using computerized colour image analysis", Eur J Dermatol, vol. 3, No. 4, pp. 299-303, May 1993.

Schindewolf, T., et al. "Classification of Melanocytic Lesions with Color and Texture Analysis Using Digital Image Processing", The International Academy of Cytology, Analytical and Quantitative Cytology and Histology, vol. 15, No. 1, pp. 1-11, Feb. 1993.

Schindewolf, T., et al. "Evaluation of different image acquisition techniques for a computer vision system in the diagnosis of malignant melanoma", Journal of the American Academy of Dermatology, vol. 31, No. 1, pp. 33-41, Jul. 1994.

Schultz et al., "Wound bed preparation: a systematic approach to wound management," Wound Repair and Regeneration, Mar./Apr. 2003, p. Sl-S28, vol. 1 1, No. 2, Supplement.

Sheehan et al., "Percent Change in Wound Area of Diabetic Foot Ulcers Over a 4-Week Period Is a Robust Predictor of Complete Healing in a 12-Week Prospective Trial," Diabetes Care, Jun. 2003, pp. 1879-1882, vol. 26, No. 6.

Sheng, Chao, Brian W. Pogue, Hamid Dehghani, Julia A. O'Hara, P. J. Hoopes, Numerical light dosimetry in murine tissue: analysis of tumor curvature and angle of incidence effects upon fluence in the tissue, Proc. SPIE, vol. 4952, 39 (2003), DOI:10.1117/12.474081, Online Publication Date: Jul. 28, 2003.

Smith & Nephew, "Leg ulcer guidelines: a pocket guide for practice," National Guideline Clearinghouse, U.S. Dept of Health & Human Services, 2002, [retrieved on Jan. 10, 2012]. Retrieved from the Internet: <URL: http://guidelines.gov/content.aspx?id=9830&search=Pressure+Ulcer>, 17 pages.

Smith & Nephew, "Visitrak Wound Measurement Device," Wound Management, [retrieved on Apr. 7, 2005]. Retrieved from the Internet: <URL: http://wound.smith-nephew.com/us/node.asp?NodeId=3 I 20>, 7 pages.

Smith & Nephew, "Guidelines for the Management of Leg Ulcers in Ireland" www.smith-nephew.com.

Smith et al., "Three-Dimensional Laser Imaging System for Measuring Wound Geometry," Lasers in Surgery and Medicine, 1998, pp. 87-93, vol. 23.

Sober, et al., "Computerized Digital Image Analysis: An Aid for Melanoma Diagnosis", The Journal of Dermatology, vol. 21, pp. 885-890, 1994.

Solomon et al., "The use of video image analysis for the measurement of venous ulcers," British J Dermatology, 1995, pp. 565-570, vol. I 33.

Steiner, A., "In vivo epiluminescence microscopy of pigmented skin lesions. II. Diagnosis of small pigmented skin lesions and early detection of malignant melanoma", Journal of the American Academy of Dermatology, vol. 17, No. 4, pp. 584-591; Oct. 1987.

Stoecker, et al. "Automatic Detection of Asymmetry in Skin Tumors", Computerized Medical Imaging and Graphics, vol. 16, No. 3, pp. 191-197, 1992.

Takiwaki, et al., "A rudimentary system for automatic discrimination among basic skin lesions on the basis of color analysis of video images", Journal of the American Academy of Dermatology, vol. 32, No. 4, pp. 600-604, Apr. 1995.

Tellez, R., "Managed Care Making Photo Documentation a Wound Care Standard," Wound Care, 1997, [retrieved on Aug. 29, 2005]. Retrieved from the Internet: <URL: http://woundcare.org/newsvol2n4/arl.htm>, 2 pages.

Thawer et al., "A Comparison of Computer-Assisted and Manual Wound Size Measurement," Ostomy Wound Management, Oct. 2002, pp. 46-53, vol. 48, No. 10.

Umbaugh et al., "Automatic Color Segmentation Algorithms with Application to Skin Tumor Feature Identification", IEEE Engineering in Medicine and Biology, pp. 75-82, Sep. 1993.

Umbaugh, et al., "An Automatic Color Segmentation Algorithm with Application to Identification of Skin Tumor Borders", Computerized Medical Imaging and Graphics, vol. 16, No. 3, pp. 227-235, May-Jun. 1992.

Umbaugh, et al., "Automatic Color Segmentation of Images with Application to Detection of Variegated Coloring in Skin Tumors", IEEE Engineering in Medicine and Biology Magazine, Dec. 1989, pp. 43-52.

Vermolen et al., "A simplified model for growth factor induced healing of circular wounds," 2005, pp. 1-15.

Voigt, H., et al. "Topodermatographic Image Analysis for Melanoma Screening and the Quantitative Assessment of Tumor Dimension Parameters of the Skin", Cancer, vol. 75, No. 4, Feb. 15, 1995.

Walker, N, Rogers A, Birchall N, Norton R, MacMahon S. Leg ulcers in New Zealand: age at onset, recurrence and provision of care in an urban population. NZ Med J; 2002; 115(1156):286-9.

Walker, N, Vandal A, Holden K, Rogers A, Birchall N, Norton R, Triggs C, MacMahon S. Does capture-recapture analysis provide more reliable estimates of the incidence and prevalence of leg ulcers in the community? Aust NZJ Public Health 2002; 26(5):451-5.

Walker, N., Rodgers A, Birchall N, Norton R, MacMahon S. The occurrence of leg ulcers in Auckland: results of a population-based study. NZ Med J; 2002: 115 (1151): 159-162.

Wallenstein et al., "Statistical analysis of wound-healing rates for pressure ulcers," Amer J Surgery, Jul. 2004 (Supplement), pp. 73S-78S, vol. 188.

Wilbright, W.A., The Use of Telemedicine in the Management of Diabetes-Related Foot Ulceration: A Pilot Study, Advances in Skin & Wound Care, Jun. 2004, [retrieved on Jul. 28, 2006]. Retrieved from the Internet: <URL: http://www.findarticles.com/p/articles/mi_qa3977/is_200406/ai_n942 . . . >, 6 pages.

Wild et al., "Wound healing analysis and measurement by means of colour segmentation," ETRS Poster Presentation V28, Sep. 15, 2005, V28-I 7, 1 page.

Williams, C., "The Verge Videometer wound measurement package," British J Nursing, Feb./Mar. 2000, pp. 237-239, vol. 9, No. 4.

Woodbury et al., Pressure ulcer assessment instruments: a critical appraisal, Ostomy Wound Management, May 1999, pp. 48-50, 53-55, vol. 45, No. 5, [retrieved on Dec. 8, 2005]. Retrieved from the Internet: <URL: http://gateway.ut.ovid.com.ezproxy.otago.ac.nzigw2/ovidweb.cgi>, 2 pages.

Woodbury, M.G., "Development, Validity, Reliability, and Responsiveness of a New Leg Ulcer Measurement Tool," Advances in Skin & Wound Care, May 2004, [retrieved on Jul. 28, 2006].

Zhao, et al, The Classification of the Depth of Burn Injury Using Hybrid Neural Network; IEEE Conference on Engineering in Medicine and Biology Society, ISBN 0-7803-2475-7; vol. 1, pp. 815-816, Sep. 1995.

Zimmet, "Venous Leg Ulcers: Evaluation and Management," American College of Phlebology. 1998.

Zuijlen, PPM., Angeles AP, Suijker MH, Kreis RW, Middelkoop E. Reliability and Accuracy of Techniques for Surface Area Measurements of Wounds and Scars. The International Journal of Lower Extremity Wounds 2004: 3(1) 7-11.

Thali, M.J., et al. "Optical 3D surface digitizing in forensic medicine: 3D documentation of skin and bone injuries." Forensic Science International. 2003.

\* cited by examiner

METHOD OF MONITORING A SURFACE FEATURE AND APPARATUS THEREFOR

CROSS-REFERENCE TO RELATED APPLICATIONS

This application is a continuation of U.S. patent application Ser. No. 15/338,216 filed Oct. 28, 2016, which is a continuation of U.S. patent application Ser. No. 15/164,793 filed May 25, 2016, now abandoned, which is a continuation of U.S. patent application Ser. No. 14/272,719 filed May 8, 2014, now U.S. Pat. No. 9,377,295, which is a continuation of U.S. application Ser. No. 12/083,491 filed May 11, 2009, now U.S. Pat. No. 8,755,053, which is a 371 U.S. National Phase of International Application No. PCT/NZ2006/000262 filed Oct. 13, 2006, which claims the benefit of New Zealand Patent Application No. 543003 filed Oct. 14, 2005, each of which is incorporated herein by reference in its entirety.

FIELD OF THE INVENTION

The invention relates to a method of monitoring a surface feature and an apparatus for performing such monitoring. The method and apparatus may find application in a wide range of fields from industrial applications through to medical or veterinary applications such as monitoring dermatological surface features such as wounds, ulcers, sores, lesions, tumours, bruises, burns, psoriasis, keloids, skin cancers, erythema etc.

BACKGROUND TO THE INVENTION

Various techniques have been used to monitor wounds, ulcers, sores, lesions, tumours etc. (herein referred to collectively as "wounds") both within hospitals and outside hospitals (e.g. domiciliary based care, primary care facilities etc.). Typically these wounds are concave and up to about 250 millimetres across. Manual techniques are typically labour-intensive and require examination and contact by skilled personnel. Such measurements may be inaccurate and there may be significant variation between measurements made by different personnel. Further, these approaches may not preserve any visual record for review by an expert or for subsequent comparison.

A number of techniques for the automated monitoring of wounds have been proposed; see for example U.S. Pat. No. 6,101,408, U.S. Pat. No. 6,873,340, U.S. Pat. No. 4,535,782 and U.S. Pat. No. 5,967,979. A common approach is to place a reference object next to the wound and determine the size of the wound utilising the scale of the reference object. It is often undesirable to place a reference object near to a wound and this requires an additional cumbersome step for a user and risks contamination of the wound. Further, when the target is not in the plane of the wound, or if the wound is not planar, there will be errors in any area calculation.

WO 2006/078902 discloses a system in which the scale of a captured image is determined using a laser triangulation sensor. The distance of the camera from a patient's skin is determined using the position of a laser spot in the image. Only a single laser spot is used and the laser is used only in a simple distance measurement.

Systems utilising stereoscopic vision and automated boundary determination are known but they are expensive, complex, bulky and require significant computational power. Further, automated identification of the boundary of a wound may be inaccurate and variable. U.S. Pat. No. 6,567,682 and US2005/0084176 use stereoscopic techniques and automated wound boundary determination requiring intensive processing and bulky equipment.

Other systems, such as that described in US2004/0136579, require the camera always to be positioned with a guide against the patient's skin. While this consistently positions the camera a desired distance from the surface to be photographed and therefore sets the scale of the image, it is unwieldy and requires undesirable contact with the skin, risking contamination of the wound.

US2005/0027567 discloses a system in which a medical professional may enter patient information into a portable computing device. A nurse may also photograph the patient's wounds, these photographs becoming part of the patient's record. However, use of this image data is limited and the computing device is effectively used simply to allow notes to be taken.

It is an object of the invention to provide a simple, inexpensive and repeatable method that does not require a scale reference object to be employed and that may be performed at remote locations or to at least provide the public with a useful choice. It is a further object of the invention to provide an apparatus that is simple, portable, inexpensive and easy to use or which at least provides the public with a useful choice.

SUMMARY OF THE INVENTION

There is thus provided a method of producing a projection of a non-planar surface feature comprising:
  a. projecting structured light onto the surface feature;
  b. capturing an image including the surface feature;
  c. determining the three-dimensional coordinates of structured light elements within the image; and
  d. unwrapping the image based on the three-dimensional coordinates of the structured light elements to produce a planar projection of the surface feature.

According to a further embodiment there is provided a method of determining the area of a non-planar surface feature comprising:
  a. projecting structured light onto the surface feature;
  b. capturing an image including the surface feature;
  c. determining the three-dimensional coordinates of structured light elements within the image;
  d. determining scale attributes for regions of the image on the basis of the three-dimensional coordinates of the structured light elements; and
  e. determining the area of the surface feature by scaling regions of the surface feature based on the scale attributes.

According to another embodiment there is provided a method of producing a projection of a surface feature comprising:
  a. capturing an image of a surface feature;
  b. determining from the image the coordinates of a plurality of points of the surface feature in three-dimensional space;
  c. determining a plane in which at least a subset of the coordinates lie; and
  d. projecting the image onto the plane to produce a transformed image.

According to a further embodiment there is provided a method of determining at least one dimension of a surface feature, including:
  a. capturing an image including a surface feature;
  b. determining a scale associated with the image;

c. manually inputting at least part of an outline of the surface feature; and
d. determining at least one dimension of the surface feature using the manually input outline data.

According to another embodiment there is provided an apparatus including:
   a. a camera for capturing an image including a surface feature; and
   b. a portable computing device including:
      i. a display configured to display the image and to allow a user to manually input at least part of an outline of the surface feature; and
      ii. a processor configured to determine a scale associated with the image and to determine at least one dimension of the surface feature using the manually input outline data.

According to a further embodiment there is provided a portable apparatus including:
   a. a camera for capturing an image of a surface feature;
   b. a portable computing device including a processor adapted to determine a scale associated with the image; and
   c. a positioning module allowing the position of the apparatus to be determined.

According to another embodiment there is provided a healthcare apparatus including:
   a. a camera for capturing an image of a surface feature on a patient;
   b. one or more auxiliary sensors for determining a physical or chemical parameter associated with the patient; and
   c. a portable computing device configured to receive image data from the camera and output from the auxiliary sensors, including a processor adapted to determine a scale associated with the image.

According to a further embodiment there is provided an apparatus including:
   a. a camera for capturing an image including a surface feature; and
   b. one or more structured light projectors configured to project structured light onto the surface, the structured light including two or more structured light components, each projected at a different angle to the camera's optical axis.

DRAWINGS

The invention will now be described by way of example with reference to possible embodiments thereof as shown in the accompanying figures in which.

DETAILED DESCRIPTION

Figure 1:
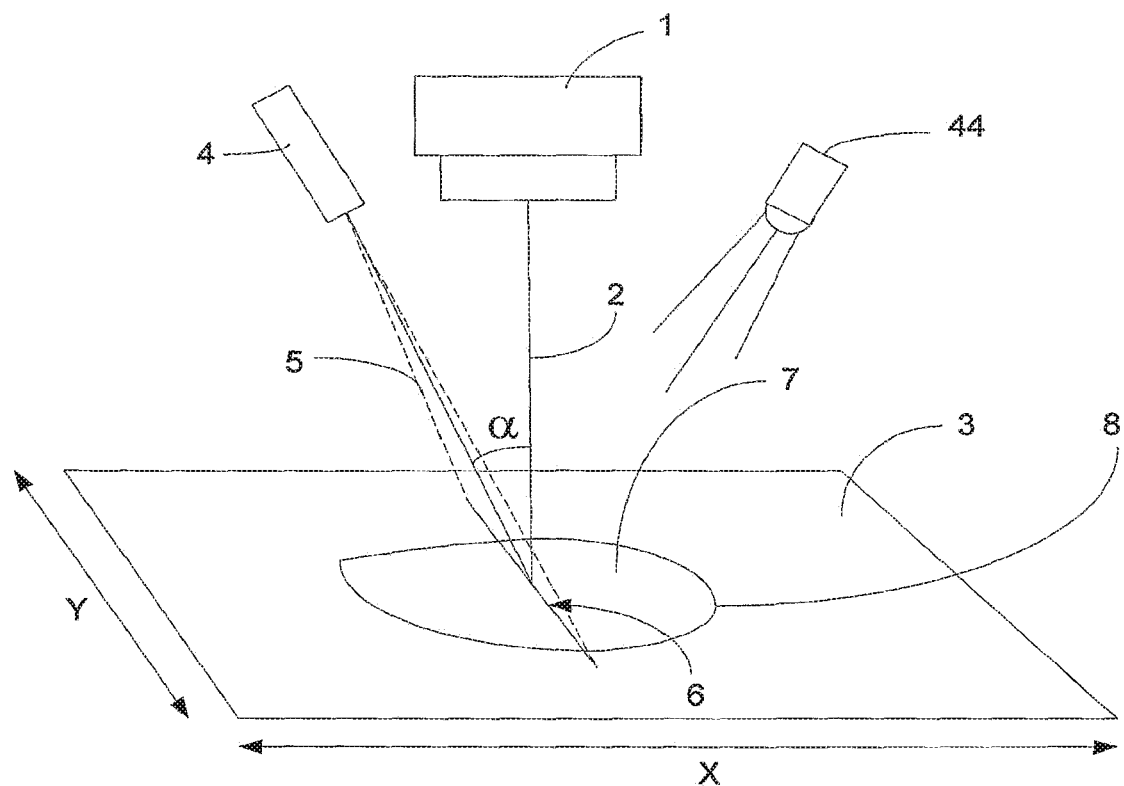
FIG. 1 shows the principle of operation of an apparatus according to one embodiment.

Referring to FIG. 1 the general principle of operation of a first embodiment of the invention will be described. A camera 1 has an optical axis 2 and an image capture region 3. Laser 4 is disposed in a fixed angular relationship to optical axis 2 so that the fan beam 5 is disposed at angle a. to optical axis 2. In this embodiment laser 4 generates a single stripe 6. Alternatively a laser projecting a single dot could be used. The camera 1 is preferably a high resolution digital colour camera. Optionally, an illumination means (such as a white LED 44 for low power applications) can be used to give relatively constant background lighting.

In use the assembly of camera 1 and laser 4 is directed so that optical axis 2 is aligned with the central region of wound 7. Laser 4 projects stripe 6 across wound 7 and the image is captured by camera 1. It will be appreciated that due to the fixed angular relationship of the laser fan beam 5 and the optical axis 2 that the distance of points of stripe 6 from camera 1 may be determined: the distance of points of stripe 6 along the x-axis shown in FIG. 1 is directly related to the distance of the point from camera 1.

In a first embodiment the assembly of camera 1 and laser 4 may be positioned above wound 7 so that stripe 6 is aligned with optical axis 2. This may be achieved by aligning cross hairs (or a dot) in the centre of a display screen displaying the image with the centre of wound 7 and stripe 6. In this way the camera is positioned a known distance away from the centre of wound 7 and so a scale can be determined.

The area of a wound may be calculated by calculating the pixel area of wound 7 from a captured image and multiplying by a known scaling factor. This technique may be effective where camera 1 can be oriented normal to the wound 7 and where wound 7 is generally planar. This technique offers a simple solution in such cases. However, many wounds are not generally planar and images may be taken at an oblique angle. In such cases this approach may not provide sufficient accuracy and repeatability due to the camera axis not being perpendicular to the wound and significant variation in the distance from the camera to the wound from that assumed.

Figure 2:
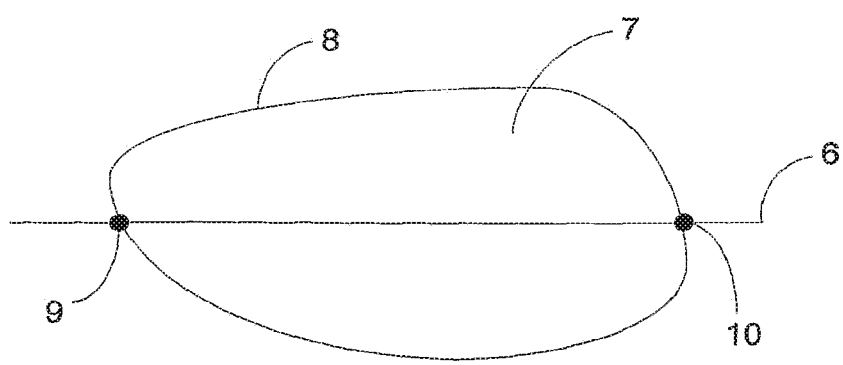
FIG. 2 shows an image of a surface feature with a single stripe projected onto the surface feature.

In a second embodiment an image may be captured in the same fashion except that the stripe need not be aligned with the optical axis of the camera. An image as shown in FIG. 2 may be obtained. Points 9 and 10, where the outline 8 of wound 7 intersects stripe 6, may be used to calculate scale. From the locations of points 9 and 10 in the image 3 their corresponding (x, y, z) coordinates can be obtained using the known relationship of the laser-camera system. Thus a scale factor may be determined based on the x,y,z coordinates of points 9 and 10 to scale the area 7 to produce a scaled value. Whilst this technique does not require a user to align the stripe with the optical axis it still suffers from the limitations of the technique described above.

Figure 3A:
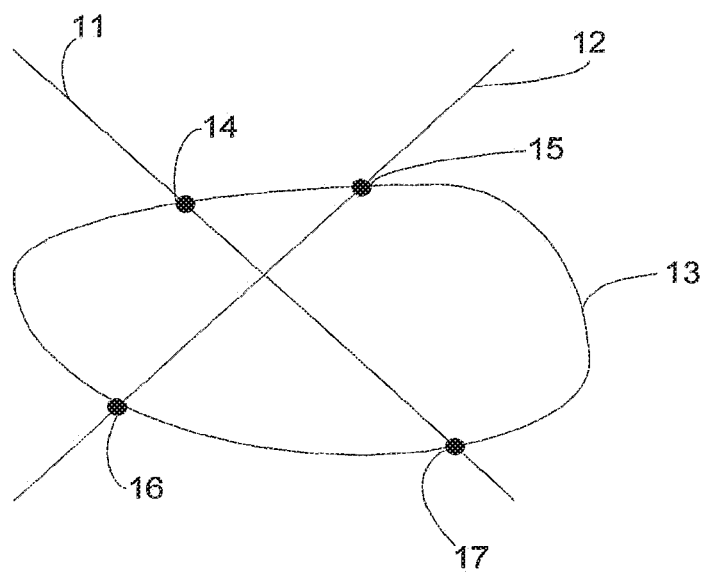
FIG. 3a shows an image of a surface feature with cross hairs projected onto the surface feature.

In one embodiment laser 4 projects structured light in the form of laser cross hairs onto the image capture area. An image captured according to this embodiment is shown in FIG. 3a. The laser stripes 11 and 12 captured in the image may be identified automatically based on colour, light intensity etc. The outline 13 is preferably user defined by drawing the outline on a touch display screen displaying the image. The image points 14, 15, 16 and 17 where cross hairs 11 and 12 intersect with outline 13 may be automatically determined. From these points their corresponding (x, y, z) coordinates can be obtained as above. These three-dimensional coordinates may be utilised to determine the best-fit plane through all points. The best-fit plane will generally be the plane having the minimum sum of squared orthogonal distances from the points to the plane. The image may then be projected onto this plane using, for example, an affine transformation. The resulting image is now scaled linearly and orthogonally. The area within outline 13 may then be calculated from this transformed image. Any number of laser stripes may be used and these stripes may intersect with each other or not.

This approach has the advantage that it provides correction where an image is not taken normal to a wound. Determining the area within a two dimensional outline rather than in three dimensional space also reduces the computational load.

Figure 3B:
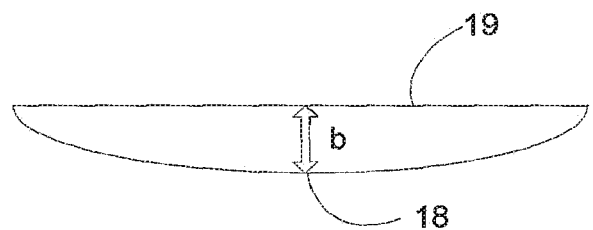
FIG. 3b shows a cross-sectional view of a wound.

A wound depth measurement may also be derived as will be explained in connection with FIG. 3b. The point 18 of greatest depth b from best-fit plane 19 may be determined iteratively or by other methods. This may be determined for an individual point along one of the cross hairs 11, 12 or for a group of points.

Utilising this information standard wound measurements may be made. The so-called "Kundin area" may be calculated by obtaining the maximum linear dimension of the wound and the short axis (orthogonal to the long axis) of the outline and multiplying the product of these measurements by $\pi/4$. The so-called "Kundin volume" may be calculated from the product of the two diameters, the maximum depth and a factor of 0.327. The dimensions may be determined and the volume calculated by a local processor. Various other algorithms may be used to calculate wound volume as appropriate for the circumstances.

Figure 4:
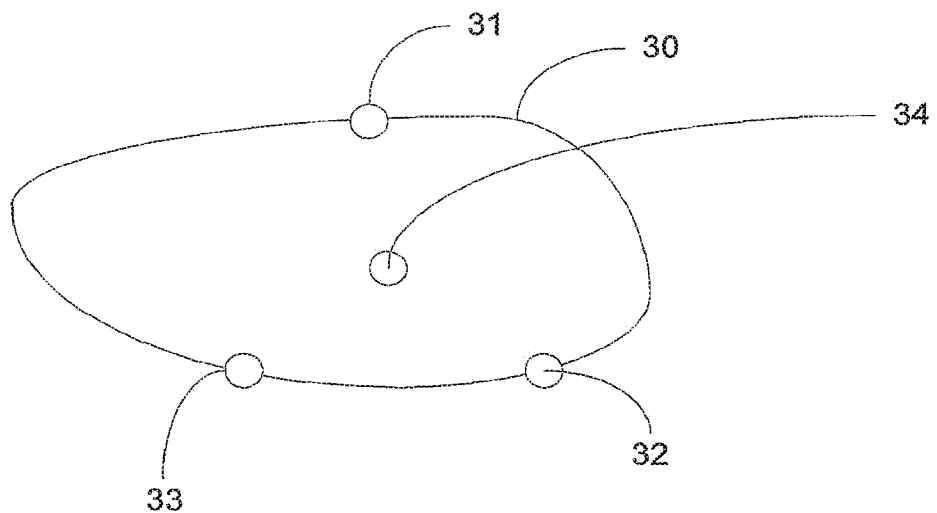
FIG. 4 shows an image of a surface feature with a series of dots projected onto the surface feature.

Referring now to FIG. 4 another implementation is shown. In this case a series of three laser dots 31, 32 and 33 are projected instead of one or more laser stripe. The laser dots are projected in a diverging pattern so that as the device is moved towards or away from the surface feature the spacing between the dots may be scaled so that they may be aligned with the outline of the wound 30. This approach has the advantage that the intersection between the stripes and the wound outline does not need to be determined as in previous embodiment. Further, the plane passing through the three points may be easily calculated. A further point 34 may be provided for depth calculation. Point 34 will preferably be placed at the position of maximum wound depth.

The outline of the wound may be determined utilising image processing techniques. However, the results of such techniques may be variable depending upon image quality, available processing capacity and the optical characteristics of the wound. According to a preferred embodiment the outline is input by a user.

Figure 5:
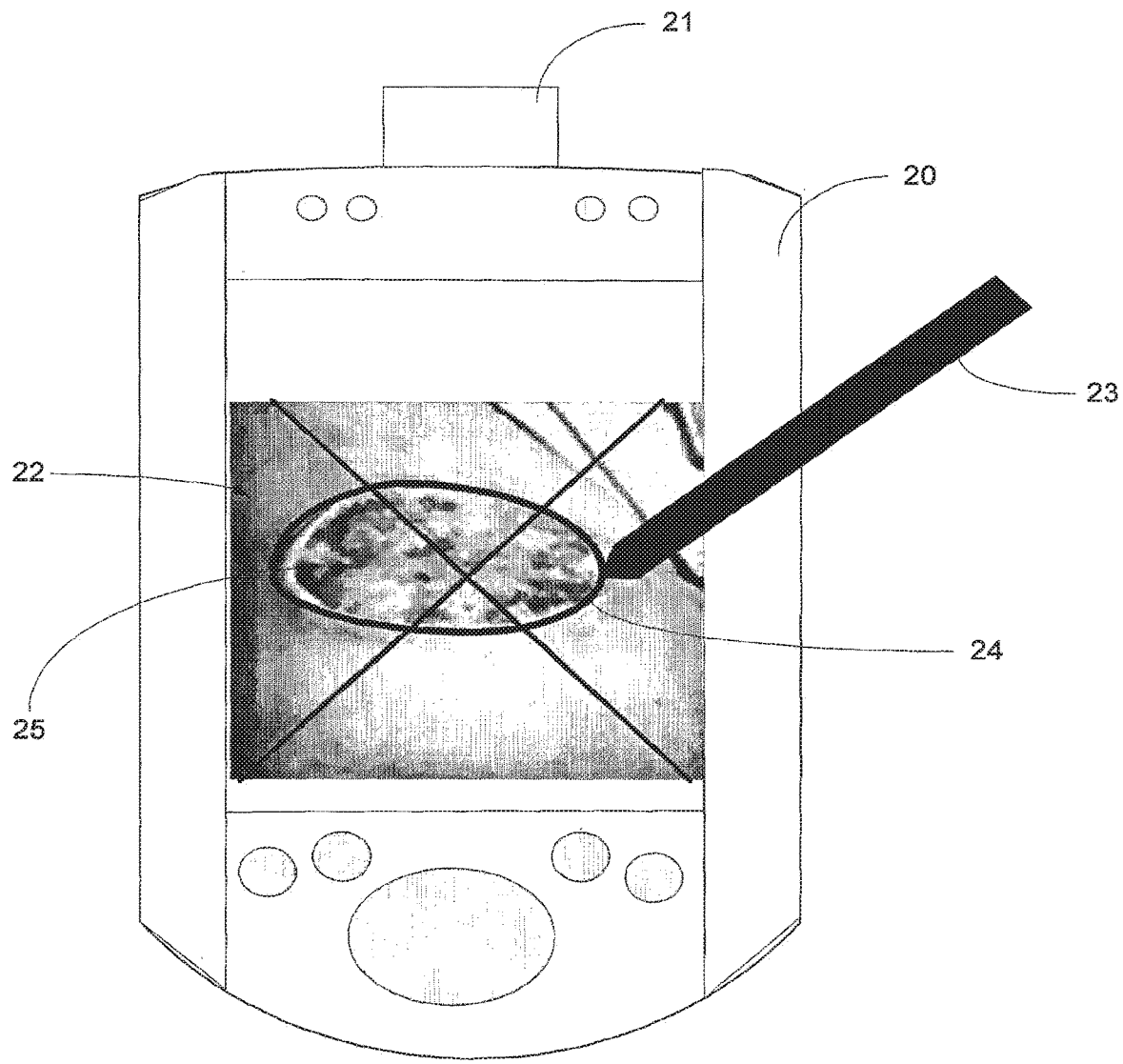
FIG. 5 shows one embodiment employing a personal digital assistant (PDA) for performing methods of the invention.

Apparatus for performing the method may take a variety of forms ranging from a stationary system (having a stationary camera or a handheld camera connected wirelessly or by a cable) to a fully portable unit. Portable units in the form of PDAs, cell phones, notebooks, ultramobile PCs etc. including an integrated or plug-in camera allow great flexibility, especially for medical services outside of hospitals. Referring now to FIG. 5 an apparatus for implementing the invention according to one exemplary embodiment is shown. The apparatus consists of a PDA 20 including a camera, such as a Palm or HP iPaQ, having a cross hair laser generator 21 which projects cross hairs at an angle to the optical axis of the PDA camera (as shown in FIG. 1). For this embodiment the cross hair laser generator may be offset from the camera by about 50 millimetres and disposed at an angle of about 30° to the optical axis of the camera. An image is captured by the camera of the PDA and displayed by touch screen 22. A user can draw an outline 24 about the boundary of the wound 25 using input device 23 on touch screen 22. The apparatus may allow adjustment of outline 24 using input device 23.

In one embodiment placing input device 23 near outline 24 and dragging it may drag the proximate portion of the outline as the input device 23 is dragged across the screen. This may be configured so that the effect of adjustment by the input device is proportional to the proximity of the input device to the outline. Thus, if the input device is placed proximate to the outline the portion proximate to the outline will be adjusted whereas if the input device is placed some distance from the outline a larger area of the outline will be adjusted as the input device is dragged.

Utilising manual input of the outline avoids the need for complex image processing capabilities and allows a compact portable unit, such as a PDA, to be utilised. Further, this approach utilises human image processing capabilities to determine the outline where automated approaches may be less effective.

Once an image is captured it may be stored by the PDA in a patient record along with measurement information (wound area, wound depth, wound volume etc.). An image without the cross hairs may also be captured by the PDA deactivating laser 21. This may be desirable where an image of the wound only is required. Where previous information has been stored comparative measurements may be made and an indication of improvement or deterioration may be provided. Where the PDA has wireless capabilities images may be sent directly for storage in a central database or distributed to medical professionals for evaluation. This allows an expert to review information obtained in the field and provide medical direction whilst the health practitioner is visiting the patient. The historic record allows patient progress to be tracked and re-evaluated, if necessary.

Measurements of other wound information may also be made. The colour of the wound and the size of particular coloured regions may also be calculated. These measurements may require a colour reference target to be placed within the image capture area for accurate colour comparison to be made.

Figure 6:
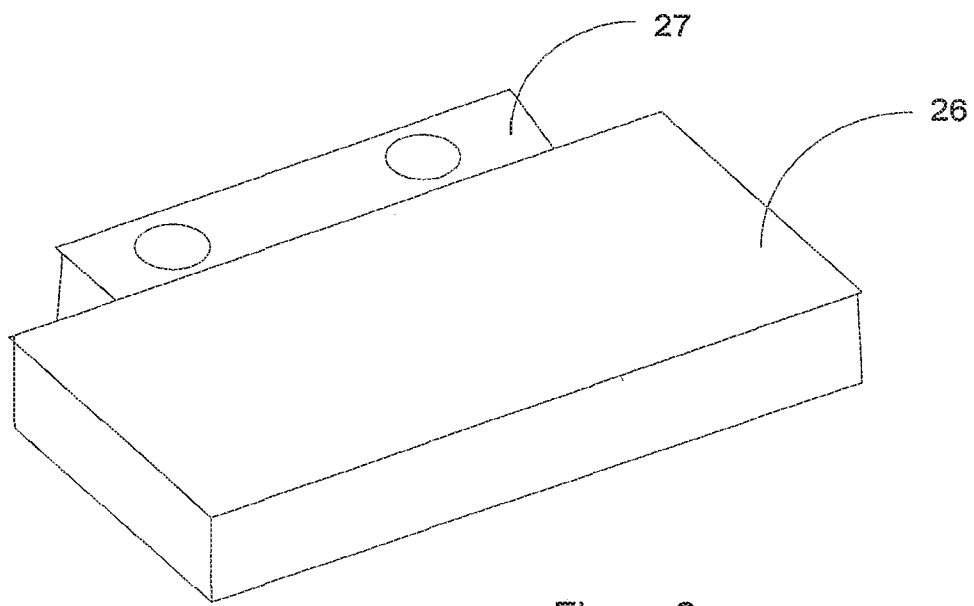
FIG. 6 shows a bottom view of a Tablet PC and 3-D camera.
Figure 7:
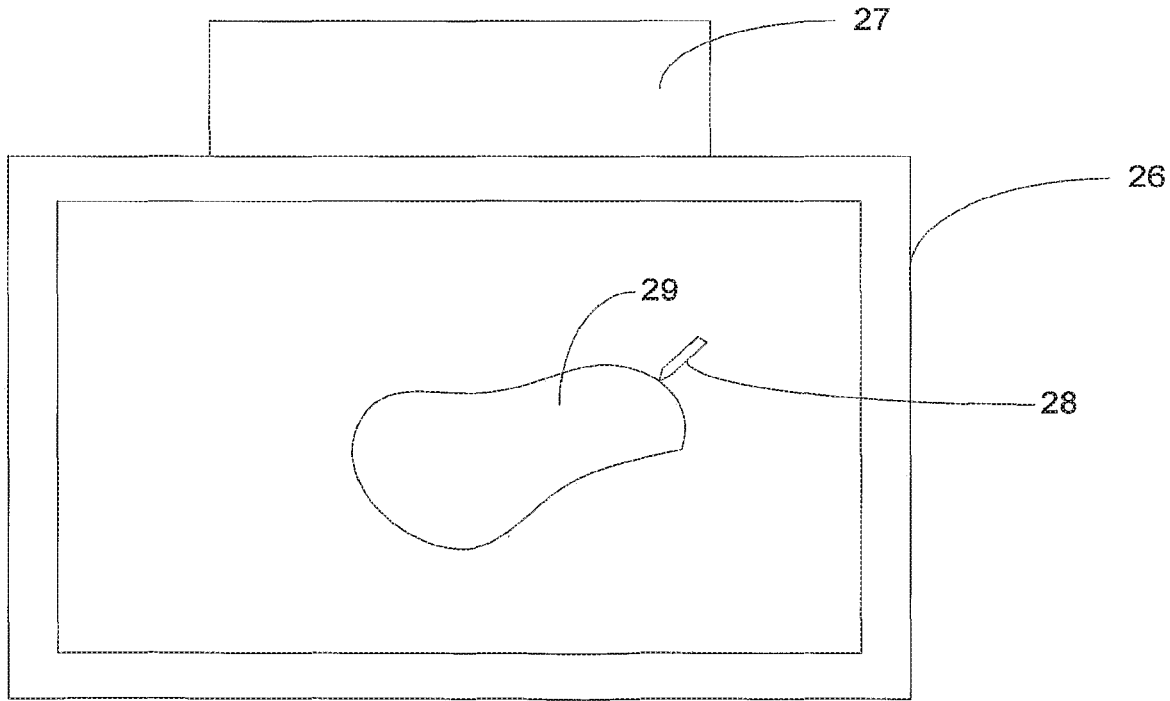
FIG. 7 shows a top view of the Tablet PC and 3-D camera of FIG. 6.

According to another embodiment a 3-D camera may be employed. FIGS. 6 and 7 show a tablet PC 26 having a stereoscopic 3-D camera 27 connected thereto. Tablet PC 26 is a notebook PC with an interactive screen such as a Toshiba Portege M200 and camera 27 may be a stereo camera such as a PointGrey Bumblebee camera. In this embodiment the stereoscopic camera 27 provides three-dimensional image information which is utilised by the tablet PC 26 to produce a three-dimensional model. However, as in the previous embodiments, a user utilising input device 28 may draw outline 29 around the wound displayed on the tablet PC screen. Utilising the three dimensional data, area and volume may be directly calculated.

In other embodiments "time-of-flight" cameras may be substituted for camera 27. Time-of-flight cameras utilise modulated coherent light illumination and per-pixel correlation hardware.

Figure 8:
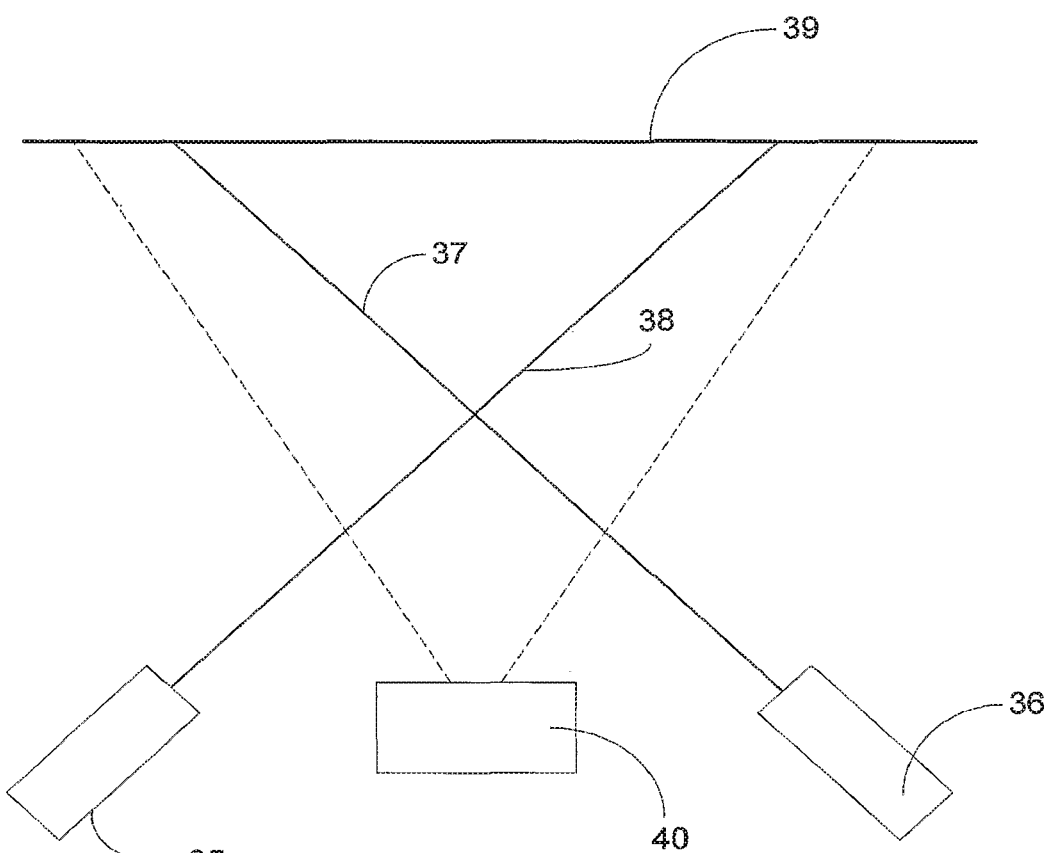
FIG. 8 shows an alternative apparatus and method.
Figure 9:
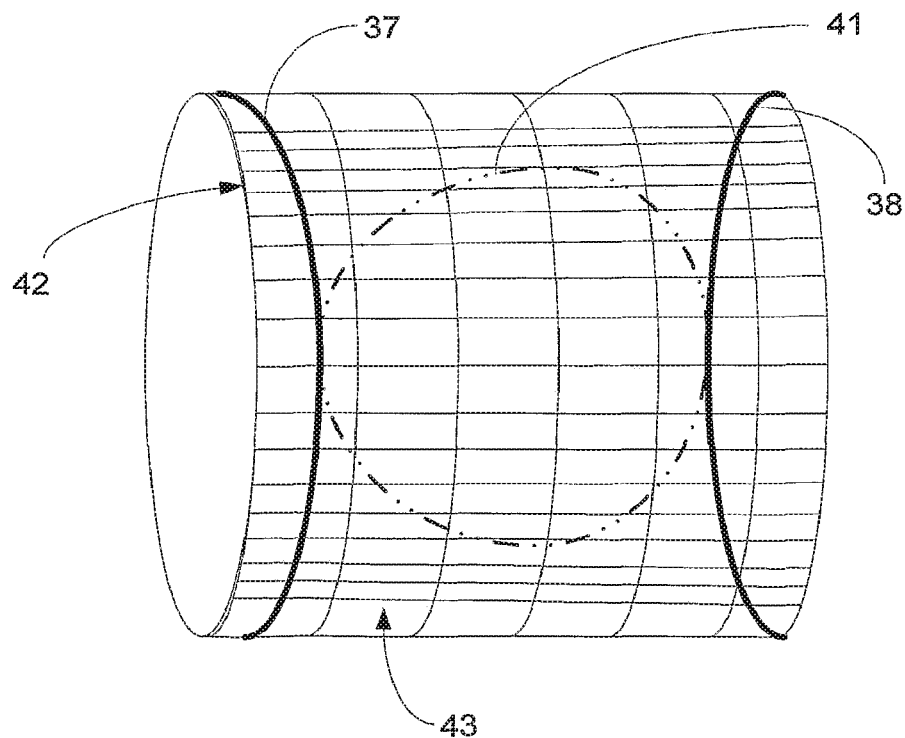
FIG. 9 shows an image illustrating a method of using the apparatus of FIG. 8.

Referring now to FIGS. 8 and 9 an alternative apparatus and method will be described. The apparatus shown in FIG.

8 includes a pair of lasers 35 and 36 which project crossing fan beams 37 and 38 onto surface 39. Lasers 35 and 36 are maintained in a fixed relationship with respect to each other and camera 40. By utilising crossing beams 37 and 38 the spacing between beams 37 and 38 may be adjusted by a user over a convenient range by moving the assembly of lasers 35, 36 and camera 40 towards or away from surface 39.

FIG. 9 illustrates use of the apparatus shown in FIG. 8 in relation to a cylindrical surface 42, such as is typical for a section of an arm or leg. The method may be applied to any surface that may be transformed to a planar (flat) form, i.e. "unwrapped". In the case of a "developable" surface, there is no distortion and the surface remains continuous, by definition. When fan beams 37 and 38 are projected onto cylindrical surface 42 they curve in a diverging manner as shown in FIG. 9. A user moves the assembly of lasers 35 and 36 and camera 40 with respect to the surface 42 so as to place beams 37 and 38 just outside the boundary 41 of a wound. Camera 40 then captures an image as shown in FIG. 9. For larger wounds the beams 37 and 38 may be within the boundary 41 of a wound.

The three-dimensional locations of elements of beams 37 and 38 may then be determined from the captured image. A three dimensional model of the surface (grid 43 illustrates this) may be calculated using the three dimensional coordinates of elements along lines 37 and 38. The model may be an inelastic surface draped between the three-dimensional coordinates of the structured light elements, or an elastic surface stretched between the three-dimensional coordinates, or a model of the anatomy, or simply a scaled planar projection. A model of the anatomy may be a model retrieved from a library of models, or simply a geometric shape approximating anatomy (a cylinder approximating a leg, for example).

In a first method the three dimensional surface may be unwrapped to form a planar image in which all regions have the same scale (i.e. for a grid the grid is unwrapped such that all cells of the image are the same size). The area within wound boundary 41 may then be easily calculated by calculating the area from the planar image.

Alternatively the area within wound boundary 41 may be calculated by scaling the areas within each region according to scale attributes associated with each region (e.g. for the grid example normalising the total area within each cell to be the same). The granularity can of course be adjusted depending upon the accuracy required.

This approach could be extended so that a plurality of parallel crossing lines are projected to achieve greater accuracy. The lines could have different optical characteristics (e.g. colour) to enable them to be distinguished. However, the two line approach described above does have the advantage of mimicking some manual approaches currently employed which involves tracing the wound outline onto a transparent sheet and then calculating the area.

Figure 10:
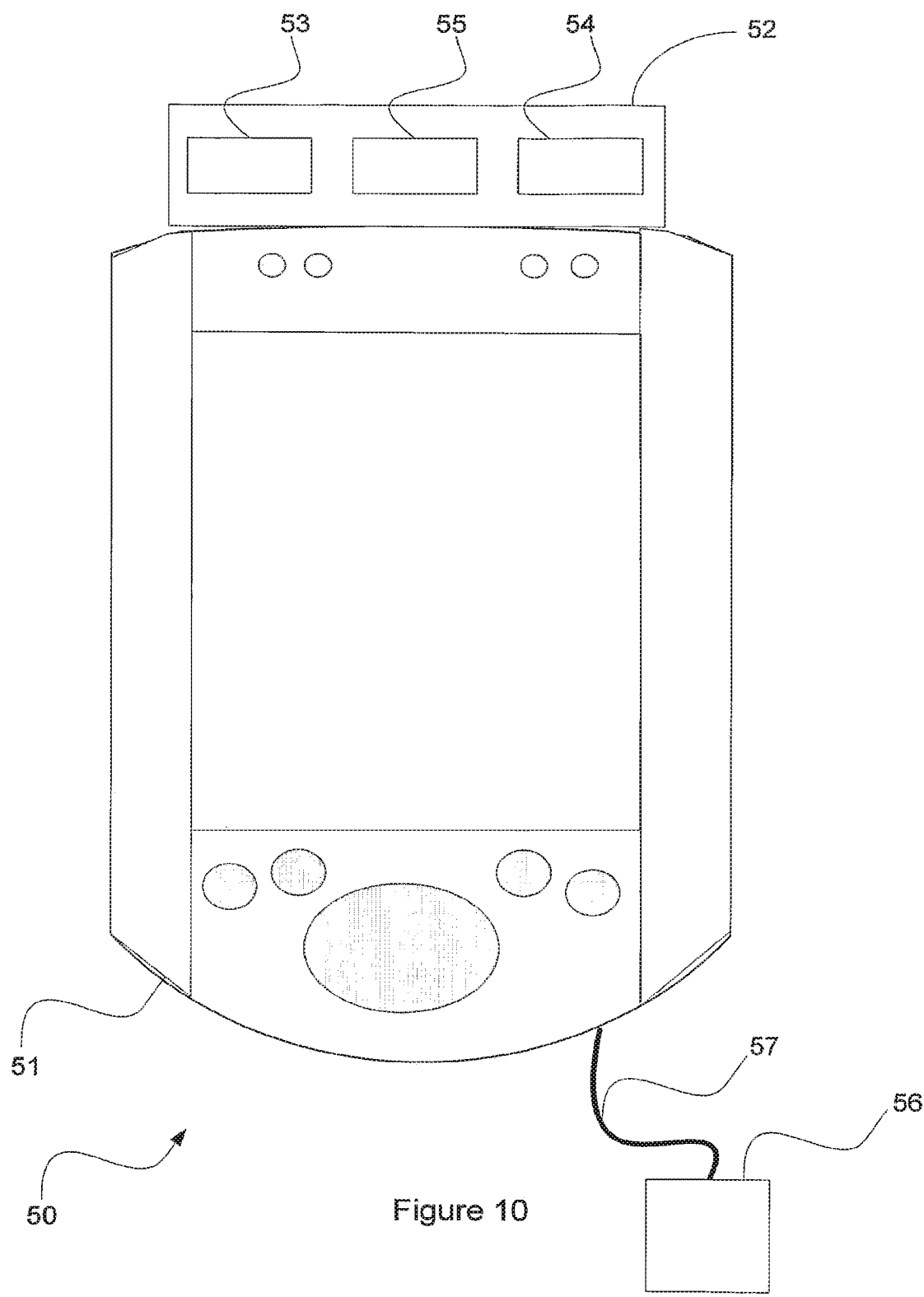
FIG. 10 shows an apparatus according to a further embodiment.

FIG. 10 shows an apparatus according to a further embodiment, in which one or more further sensors are provided. The apparatus 50 includes a PDA 51, with a housing 52 containing a camera 53, laser generator 54 and a GPS receiver 55. The GPS receiver may alternatively be provided in a separate module, within the PDA 51 or in a plugin card. When external to the PDA, the positioning module may be connected to the PDA via any suitable wired or wireless connection. Positioning systems other than GPS may also be suitable.

Use of a positioning system allows automation of tasks and validation of actions. This may be achieved using the apparatus alone, or through communication with a central computer system and database. For example, a nurse may be using the apparatus to monitor wound healing for a patient. The nurse arrives at the patient's home and the position of the home is determined using the GPS system. The position may be used in determining an address. This may be used to ensure that the nurse is at the correct address, possibly by comparison with a schedule of patient visits.

In response to determination of an address, the system may automatically select a patient associated with that address from a patient database. Alternatively, for a new patient, the nurse enters patient information using the PDA and this information is automatically associated with the address determined using the GPS receiver. This avoids the necessity to enter a large amount of data using the PDA. Similarly, the position may be used directly without converting to an address, to select a patient associated with that position, or to associate a new patient with a position.

The positioning system may also be used in auditing user actions. For example, a nurse may enter patient information and this may be verified using the position data by checking it against a patient database. This also allows an employer to monitor staff actions, to ensure that a staff member has in fact visited a particular address or patient.

Data gathered using the GPS system may also be stored for future reference. For example, travel data may be gathered by monitoring position information over a period of time. This data may be used later in estimating travel times between sites and in establishing or optimizing travel schedules for workers.

FIG. 10 also shows an auxiliary sensor 56, connected to the PDA via a wired connection 57. A wireless connection may also be used and any number of auxiliary sensors may be connected to the PDA. Auxiliary sensors could also be included in the module 52. The auxiliary sensor allows further data to be gathered. For example, where the apparatus is used to capture an image of a wound in a patient's skin, the auxiliary sensor will allow measurement of another physical or chemical parameter associated with the patient, such as temperature, pH, moisture or odour. The auxiliary sensor may also be an optical probe, which illuminates the skin or wound and analyses the spectrum of scattered light. For example, a fluorescence probe could be used.

In one embodiment the auxiliary sensors include a Doppler Ultrasound Probe. The management of some types of wound, such as vascular ulcers, requires measurement of blood-flow in the underlying tissue and Doppler Ultrasound is the method generally used to perform this measurement. Low-power Doppler Ultrasound Probes such as those used in foetal heart-beat monitors may be suitable. This would make it unnecessary for a patient to visit a clinic or hospital, or for a separate ultrasound machine to be transported.

Data gathered from the auxiliary sensors may be associated with a particular address, patient or image. Data may be displayed on the PDA's screen, and may be overlaid on the associated image. The combined information may enable more advanced wound analysis methods to be employed.

Use of auxiliary sensors allows many measurements to be more easily performed at the same time as an image is captured and by the same person. (In a medical setting, this person may also be performing wound treatment.) This is efficient and also allows data to be easily and accurately associated with a particular image or patient.

In any of the above embodiments the section containing the lasers and camera could be combined so that they can be housed in a detachable unit from the PDA, interfaced via a SDIO or Compact Flash (CF) slot, for example. This allows added convenience for the user, plus enables lasers and cameras to be permanently mounted with respect to each other, for ease of calibration. Furthermore, the camera can be optimally focussed, and an illumination means, such as a white LED, may be used to give relatively constant background lighting.

In any of the above embodiments the section containing the camera and/or lasers could be movable with respect to the PDA (being interconnected by a cable or wirelessly). This allows independent manipulation of the camera to capture wounds in awkward locations whilst optimising viewing of the image to be captured.

In any of the embodiments described above, multiple images may be captured in rapid succession. This is particularly advantageous where structured light (e.g. a laser) is used. For example, two images may be captured: one with the laser on and one with the laser off. Subtracting one of these images from the other yields an image with just the laser lines (disregarding the inevitable noise). This facilitates the automated detection of the laser profiles. Other combinations of images may also be useful. For example, three images could be captured: one without illumination but with the laser on, one without illumination and with the laser off and a third image with the illumination on and the laser off. The first two images could be used to detect the laser profile, while the third image is displayed to the user. The first image, showing the laser line with the illumination off would have a higher contrast, so that the laser line would stand out more clearly. Capturing the images in rapid succession means that the motion of the camera between the images is negligible.

Figure 11:
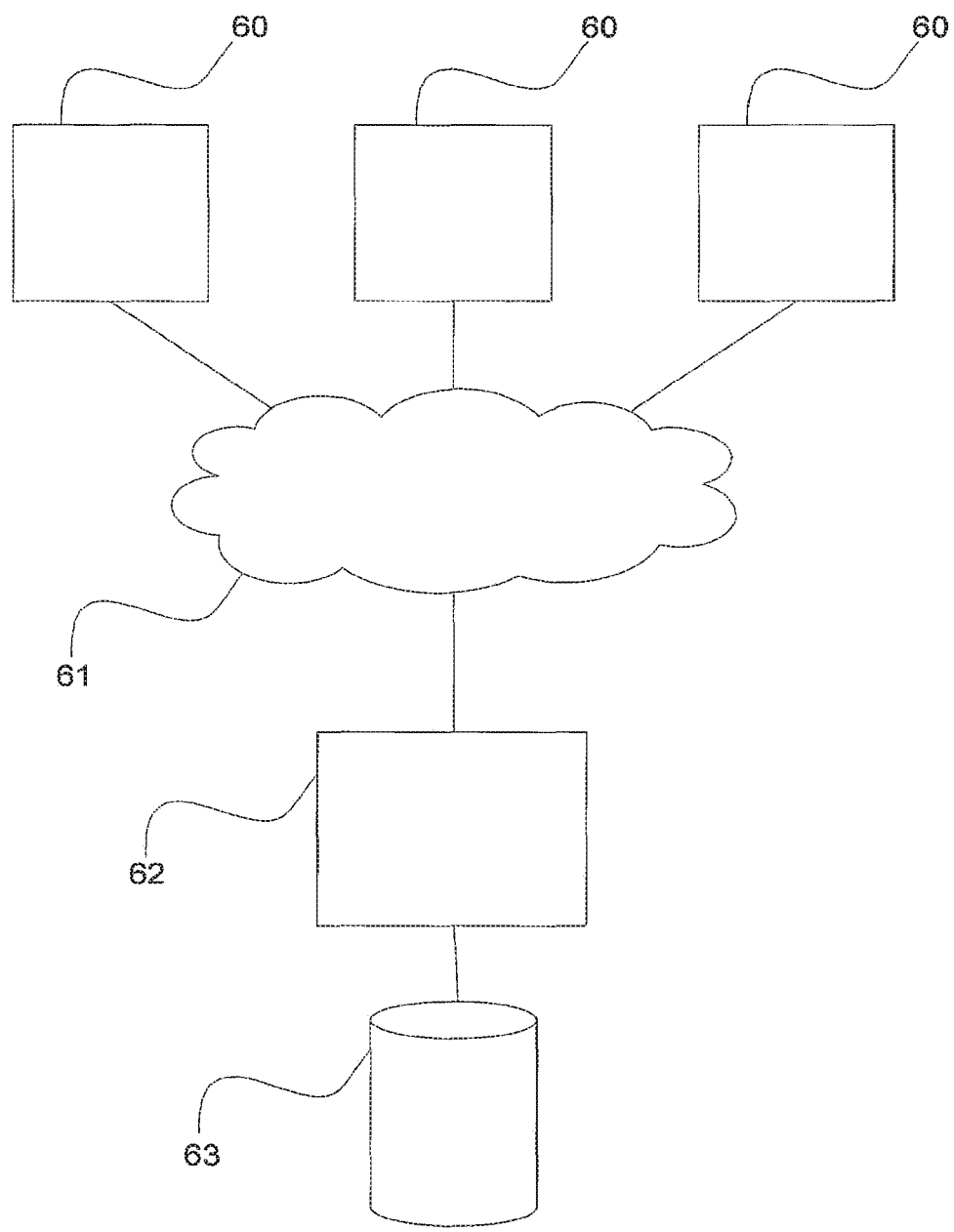
FIG. 11 shows a system according to another embodiment.

FIG. 11 shows a system including one or more portable apparatuses 60 such as those described above. These apparatuses 60 may communicate via a communication network 61 with a central server 62. Preferably the apparatuses 60 communicate wirelessly with the server 62. The central server 62 may utilize an external database 63 for data storage.

This centralised system allows appropriate categorising and storage of data for future use. For example, by mining historical data from the database it is possible to analyse the efficacy of a particular treatment or to compare different treatments. Statistical trends of conditions, treatments and outcomes can be monitored. This data can be used to suggest a particular treatment, based on a set of symptoms exhibited by a particular patient. Data can provide predictions for wound healing. Where actual healing differs from the prediction by more than a threshold, the system may issue an alert.

A healthcare provider can use the data to audit efficiency of its whole organisation, departments within the organisation or even individual workers. Historical data may be compared with historical worker schedules to determine whether workers are performing all tasks on their schedules. Efficiencies of different workers may be compared.

There are thus provided methods of measuring wounds that are simple, inexpensive, repeatable and may be performed remotely. The methods utilize human image processing capabilities to minimise the processing requirements. The methods do not require the placement of articles near the wound and allow historical comparison of a wound. The apparatus are portable with relatively low processing requirements and enable records to be sent wirelessly for evaluation and storage.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

We claim:

1. A computer-implemented method for evaluating a wound on a human or veterinary patient, the method comprising:
   capturing image data characterizing the wound with an image sensor of a portable computing device configured to be held and operated in a user's hand at a position relative to the wound;
   capturing depth data characterizing the wound from a structured light device carried by and operatively coupled to the portable computing device at the position;
   determining an area of the wound and at least one of a depth of the wound and a volume of the wound based on the image data and the depth data; and
   displaying the area and the at least one of the depth and the volume of the wound on a display of the portable computing device.

2. The method of claim 1 wherein the image data and the depth data are captured at the same time or in rapid succession with negligible motion of the portable computing device between captures.

3. The method of claim 1, further comprising determining an outline of the wound using the image data, and wherein determining the area is based on the outline.

4. The method of claim 3 wherein determining the outline of the wound includes automatically generating the outline using the image data.

5. The method of claim 3 wherein determining the outline of the wound includes receiving, at the portable computing device, data characterizing a user-drawn outline of the wound.

6. The method of claim 1, further comprising comparing at least one of the area of the wound, the depth of the wound, or the volume of the wound with a previously-obtained area of the wound, a previously-obtained depth of the wound, or a previously-obtained volume of the wound, respectively.

7. The method of claim 1 wherein determining the area and the at least one of the depth and the volume of the wound is performed by the portable computing device.

8. The method of claim 1 wherein determining the area and the at least one of the depth and the volume of the wound is performed by a remote server in communication with the portable computing device.

9. The method of claim 1, further comprising generating a three-dimensional model of the wound.

10. The method of claim 1 wherein the structured light device and the portable computing device are separate components, and wherein the structured light device is operatively coupled to the portable computing device via a wired connection.

11. The method of claim 1 wherein the image sensor is integrated with the portable computing device.

12. The method of claim 1 wherein the wound is disrupting the skin of the living patient, and wherein the depth is the depth of the bottom surface of the wound relative to the skin at a boundary of the wound.

13. The method of claim 1, further comprising determining an outline of the wound, the outline defining an outer boundary of the wound, wherein the area is the area bound by the outline, and wherein the depth is the distance between a bottom surface of the wound and a plane defined by a plurality of points on the outline.

14. The method of claim 1 wherein the wound comprises an ulcer, a sore, a lesion, or a tumor.

15. The method of claim 1, further comprising generating a suggested treatment for the wound based on at least one of the area and the at least one of the depth and the volume, the suggested treatment being generated by one of either the portable computing device or a remote server in communication with the portable computing device.

16. The method of claim 1 wherein the depth data comprises a set of three-dimensional coordinates, and wherein the depth or the volume of the wound is determined from a three-dimensional model of the wound derived from the three-dimensional coordinates.

17. A non-transitory computer-readable storage medium encoded with instructions that, when executed by a processor, causes the processor to perform a method for evaluating a wound on a living human or veterinary patient, the method comprising:
   capturing image data characterizing the wound with an image sensor of a portable computing configured to be held and operated in a user's hand at a position relative to the wound;
   capturing depth data characterizing the wound from a structured light device carried by and operatively coupled to the portable computing device at the position;
   determining an area of the wound and at least one of a volume of the wound and a depth of the wound based on the image data and the depth data; and
   displaying the area and the at least one of the depth and the volume of the wound on a display of the portable computing device.

18. The non-transitory computer-readable storage medium of claim 17 wherein the image data and the depth data are captured at the same time or in rapid succession with negligible motion of the portable computing device between captures.

19. The non-transitory computer-readable storage medium of claim 17, the method further comprising determining an outline of the wound using the image data, and wherein determining the area is based on the outline.

20. The non-transitory computer-readable storage medium of claim 19 wherein determining the outline of the wound includes automatically generating the outline using the image data.

21. The non-transitory computer-readable storage medium of claim 19 wherein determining the outline of the wound includes receiving, at the portable computing device, data characterizing a user-drawn outline of the wound.

22. The non-transitory computer-readable storage medium of claim 19, the method further comprising storing at least one of the image data, the depth data, the area of the wound, the at least one of the depth and the volume of the wound, and the outline of the wound at a database remote from the portable computing device.

23. The non-transitory computer-readable storage medium of claim 17, the method further comprising comparing at least one of the area of the wound, the depth of the wound, and the volume of the wound, with a previously obtained area of the wound, a previously obtained depth of the wound, or a previously obtained volume of the wound, respectively.

24. The non-transitory computer-readable storage medium of claim 17 wherein determining the area and the at least one of the depth and the volume of the wound is performed by the portable computing device.

25. The non-transitory computer-readable storage medium of claim 17 wherein determining the area and the at least one of the depth and the volume of the wound is performed by a remote server in communication with the portable computing device.

26. The non-transitory computer-readable storage medium of claim 17 wherein the wound is disrupting the skin of the living patient, and wherein the depth is the depth of the bottom surface of the wound relative to the skin at a boundary of the wound.

27. The non-transitory computer-readable storage medium of claim 17, the method further comprising generating a suggested treatment for the wound based on at least one of the area and the at least one of the depth and the volume, the suggested treatment being generated by one of either the portable computing device or a remote server in communication with the portable computing device.

28. A computer-implemented method for evaluating a wound of a living human or veterinary patient, the method comprising:
   capturing image data characterizing the wound from an image sensor of a portable computing device configured to be held and operated in a user's hand at a position relative to the wound;
   capturing depth data characterizing the wound from a structured light device carried by and operatively coupled to the portable computing device at the position;
   determining at least one of an area of the wound and at least one of a depth of the wound and a volume of the wound based on the image data and the depth data;
   displaying the at least one of the area, volume, and depth of the wound on a display of the portable computing device; and
   comparing the at least one area, depth, and volume to a previously-obtained area, a previously-obtained depth, or a previously-obtained volume measurement, respectively, that characterizes the wound of the patient at an earlier time.

29. The method of claim 28 wherein the image data and the depth data are captured at the same time or in rapid succession with negligible motion of the portable computing device between captures.

30. The method of claim 28, further comprising generating a suggested treatment for the wound based on the comparison, the suggested treatment being generated by one of either the portable computing device or a remote server in communication with the portable computing device.

31. A method for monitoring healing of a wound of a living human or veterinary patient, the method comprising:
   capturing image data characterizing the wound at a plurality of time points using at least one image sensor of a portable computing device configured to be held and operated in a user's hand at a position relative to the wound;
   capturing depth data characterizing the wound at the plurality of time points using at least one structured light device carried by and operatively coupled to the portable computing device at the position; and
   transmitting the image data from the image sensor and the depth data from the structured light device to at least one computing device, wherein the at least one computing device— determines an area of the wound at each of the plurality of time points based on the image data, determines at least one of a depth of the wound and a volume of the wound at each of the plurality of time points based on the depth data, and provides an indication of an improvement or a deterioration of the wound.

32. The method of claim 31 wherein the image data and the depth data are captured at the same time or in rapid succession with negligible motion of the portable computing device between captures.

33. The method of claim 31, further comprising determining a treatment plan for the wound based on the improvement or deterioration.

34. The method of claim 31, further comprising analyzing the efficacy of a treatment applied to the wound before and/or during the plurality of time points.

* * * * *